US007858650B2

(12) United States Patent
Yamamoto et al.

(10) Patent No.: US 7,858,650 B2
(45) Date of Patent: Dec. 28, 2010

(54) MEDICINAL COMPOSITION FOR INHALATION

(75) Inventors: Shigeki Yamamoto, Mishima-gun (JP);
Tsutomu Shiroya, Mishima-gun (JP);
Michiaki Kadode, Mishima-gun (JP);
Toru Maruyama, Mishima-gun (JP);
Kousuke Tani, Mishima-gun (JP);
Toshihiko Nagase, Mishima-gun (JP)

(73) Assignee: Ono Pharmaceutical Co., Ltd., Osaka (JP)

( * ) Notice: Subject to any disclaimer, the term of this patent is extended or adjusted under 35 U.S.C. 154(b) by 765 days.

(21) Appl. No.: 11/665,966

(22) PCT Filed: Oct. 21, 2005

(86) PCT No.: PCT/JP2005/019376

§ 371 (c)(1),
(2), (4) Date: Apr. 20, 2007

(87) PCT Pub. No.: WO2006/043655

PCT Pub. Date: Apr. 27, 2006

(65) Prior Publication Data

US 2008/0114043 A1    May 15, 2008

(30) Foreign Application Priority Data

Oct. 22, 2004    (JP) .............................. 2004-307902

(51) Int. Cl.
*A61K 31/427*    (2006.01)
*C07D 277/36*    (2006.01)

(52) U.S. Cl. ........................................ 514/369; 548/188
(58) Field of Classification Search ................. 514/369; 548/183

See application file for complete search history.

(56) References Cited

U.S. PATENT DOCUMENTS

| 4,039,668 | A | 8/1977 | Fuchs |
| 6,723,713 | B2 | 4/2004 | Sequeira |
| 7,402,605 | B2 * | 7/2008 | Tani et al. .................... 514/424 |
| 2002/0124577 | A1 | 9/2002 | Ferris et al. |
| 2002/0189610 | A1 | 12/2002 | Bozung et al. |
| 2005/0020686 | A1 | 1/2005 | Maruyama |
| 2009/0042885 | A1 * | 2/2009 | Tani et al. ................ 514/236.8 |

FOREIGN PATENT DOCUMENTS

| EP | 0860430 A2 | 8/1998 |
| JP | 50-047967 A | 4/1975 |
| JP | 09-501700 A | 2/1997 |
| JP | 2004-517942 A | 6/2004 |
| NL | 7704739 A | 11/1977 |
| WO | 02/42268 A2 | 5/2002 |
| WO | 03/008377 A1 | 1/2003 |
| WO | WO 03/009872 A1 | 2/2003 |
| WO | WO 03/074483 A1 | 9/2003 |
| WO | WO 2004/065365 A1 | 8/2004 |
| WO | WO 2005/053707 A1 | 6/2005 |
| WO | WO 2005/061492 A1 | 7/2005 |

OTHER PUBLICATIONS

Vippagunta et al., Crystalline solids, 2001, Advanced Drug Delivery Reviews, 48, 3-26.*
Mitsuo Matsumoto; "Yakuzaigaku Manual", Nanzando, 1989, pp. 30, 118-119.
Hitoshi Sezaki, "Drug Delivery System", Nankodo co., Ltd., pp. 49 to 57.
Mitsuru Hashida, "Keiko Toyo Seizai no Sekkei to Hyoka", Kabushiki Kaisha Yakugyo Jihosha, 1995, pp. 216 to 231.
Burgess, Janette K. et al. "Increased sensitivity of asthmatic airway smooth muscle cells to prostaglandin E2 might be mediated by increase numbers of E-prostanoid receptors" Journal of Allergy and Clinical Immunology, vol. 113, No. 5. May 2004, p. 876-881, XP009123804.
Billot, Xavier et al. "Discovery of a Potent and Selective Agonist of the Prostaglandin EP4 Receptor" Bioorganic & Medicinal Chemistry Letters, Pergamon, Elsevier Science, GB, vol. 13, No. 6, Mar. 24, 2003, p. 1129-1132, XP002471705.
Zoretic, P.A. et al. "Synthesis of (E)-7-[[2-[4-(m-Trifluoromethylphenoxy)-3α and 3β-Hydroxy-1-butenyl]-5-oxo-1-pyrrolidinyl]]heptanoic Acids" Journal of Heterocyclic Chemistry, Heterocorporation, Provo, US. vol. 20, Jan. 1, 1983, p. 465-466, XP002182343.
Extended European Search Report issued in European Patent Application No. 05795486.9-2404 dated Nov. 2.

* cited by examiner

*Primary Examiner*—Kamal A Saeed
*Assistant Examiner*—Kristin Bianchi
(74) *Attorney, Agent, or Firm*—Sughrue Mion, PLLC

(57) ABSTRACT

A medicinal composition for inhalation containing a continuous-release type prodrug of an EP2 agonist topically exhibits a prolonged bronchodilating and antiinflammatory effects. Namely, the medicinal composition for inhalation containing a continuous-release type prodrug of an EP2 agonist is useful as a safe preventive and/or a remedy for respiratory diseases (for example, asthma, pulmonary injury, pulmonary fibrosis, pulmonary emphysema, bronchitis, chronic obstructive pulmonary disease, adult respiratory distress syndrome, cystic fibrosis, pulmonary hypertension or the like) without causing any systemic effect such as lowering blood pressure. Thus, a safe and useful remedy for respiratory diseases is provided.

5 Claims, 5 Drawing Sheets

MEDICINAL COMPOSITION FOR INHALATION

TECHNICAL FIELD

The present invention relates to a pharmaceutical composition for inhalation comprising EP2 agonist.

For more detail, it relates to a pharmaceutical composition for inhalation comprising a sustained prodrug of EP2 agonist which is long-acting and reduces hypotensive effect. Concretely, it relates to a pharmaceutical composition for inhalation comprising a compound represented by formula (I):

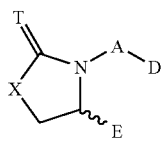

wherein all symbols have the same meanings as described below, a salt thereof, a solvate thereof or a cyclodextrin clathrate thereof.

BACKGROUND ART

Chronic obstructive pulmonary disease (COPD) is one of the respiratory diseases and is a disease accompanying airflow obstruction in addition to chronic bronchitis, emphysema, or the complications of both diseases, and characterized by airflow limitation which is not completely reversible. Smoking or the like triggers inflammation of the bronchus or collapse of alveoli. As a result, symptoms such as cough, sputum production or shortness of breath appear, and when the disease progresses, hypoxemia will be developed. As an agent for treating COPD, a bronchodilator (for example, an anticholinergic drug, a $\beta_2$-stimulator, a xanthine derivative or the like), an expectorant, a steroid or an antibiotic is used. With the use of a bronchodilator or an expectorant, improvement of the symptoms can be expected, however, they are not agents that fundamentally improve the pathological conditions. Additionally, long-term dosing of a steroid is not preferable in terms of side effects or the like. Accordingly, a safe and useful therapeutic agent for COPD has been demanded.

It is known that the compound described in WO03/74483 (Patent Reference 1) has EP2 agonist action and is useful for prevention and/or treatment of pulmonary injury, pulmonary fibrosis, pulmonary emphysema, bronchitis, chronic obstructive pulmonary disease etc.

However, since EP2 agonist acted on organs besides the respiratory organ, for example circulatory organs, there was fear that it lower the blood pressure of the patient having the normal blood pressure.

[Patent Reference 1] WO2003/74483

DISCLOSURE OF THE INVENTION

Problems to be Solved by the Invention

An object of the present invention is to provide a safe and effective medicament which has bronchodilating and anti-inflammatory effect to treat respiratory disease.

Means for Solution of a Problem

The inventors of the present invention carried out intensive studies for the purpose of solving the above problems. As a result, they found that by administering an EP2 agonist by inhalation, a bronchodilating effect and an anti-inflammatory effect are locally exhibited and an undesired effect of the EP2 agonist, for example, an effect on circulatory organs such as a hypotensive effect can be avoided or reduced.

Additionally, the inventors of the present invention also found that as an EP2 agonist in which a desired effect in the respiratory organ can be sustained and an effect on circulatory organs can be avoided or reduced, a carboxylic acid prodrug is favorable. The inventors of the present invention particularly found that a prodrug having an ester with a high lipid-soluble long-chain aliphatic alcohol or an amide with a long-chain aliphatic amine remains in an affected area in the respiratory organ and exhibits its effect in a sustained manner for a long period of time. Namely, an inhaled prodrug of the above-mentioned EP2 agonist in an inactive form remains in an affected area, and since the ester with a long-chain aliphatic alcohol or the like is not susceptible to enzymatic digestion, the inactive form of EP2 agonist is gradually changed into an active form of EP2 agonist, and the desired effect is sustained in the desired organ for a long period of time. Furthermore, by inhalation of the prodrug, since the concentration of the EP2 agonist does not increase transiently, an effect on circulatory organs is avoided and a hypotensive effect can be reduced.

Additionally, with regard to an oral pharmaceutical composition, a prodrug is sometimes used for the purpose of increasing the oral absorption of an agent. However, the inventors of the present invention found an amazing effect that the effect is sustained in the respiratory organ and the hypotensive effect is reduced, which is an object completely different from that of the oral pharmaceutical composition, by using a sustained prodrug in a pharmaceutical composition for inhalation.

Therefore, they have found that EP2 agonist, particularly a pharmaceutical composition for inhalation comprising a sustained prodrug of EP2 agonist has bronchodelating and anti-inflammatory effect and it can be a safe and effective medicament, and have completed the present invention.

That is, the present invention relates to the followings.

1. A pharmaceutical composition for inhalation comprising EP2 agonist;
2. The pharmaceutical composition according to above 1, wherein the EP2 agonist is a sustained prodrug;
3. The pharmaceutical composition according to above 2, wherein the prodrug has reduced hypotensive effect;
4. The pharmaceutical composition according to above 2, wherein the prodrug is an ester of a long chain aliphatic alcohol or an amide of a long chain aliphatic amine;
5. The pharmaceutical composition according to above 1, wherein the EP2 agonist is a compound represented by formula (I):

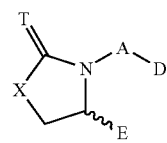

wherein T is (1) an oxygen atom or (2) a sulfur atom,
X is (1) —CH$_2$— (2) —O— or (3) —S—,
A is A$^1$ or A$^2$,
A$^1$ is (1) C2-8 straight-chain alkylene optionally substituted by 1 to 2 C1-4 alkyl, (2) C2-8 straight-chain alkenylene optionally substituted by 1 to 2 C1-4 alkyl or (3) C2-8 straight-chain alkynylene optionally substituted by 1 to 2 C1-4 alkyl, $A^2$ is $-G^1-G^2-G^3$, $G^1$ is (1) C1-4 straight-chain alkylene optionally substituted by 1 to 2 C1-4 alkyl, (2) C2-4 straight-chain alkenylene optionally substituted by 1 to 2 C1-4 alkyl or (3) C2-4 straight-chain alkynylene optionally substituted by 1 to 2 C1-4 alkyl, $G^2$ is (1) —Y—, (2) -ring 1-, (3) —Y-ring 1-, (4) -ring 1-Y— or (5) —Y—C1-4 alkylene-ring 1-, Y is (1) —S—, (2) —SO—, (3) —SO$_2$—, (4) —O— or (5) —NR$^1$—, $R^1$ is (1) a hydrogen atom, (2) C1-10 alkyl or (3) C2-10 acyl, $G^3$ is (1) a bond, (2) C1-4 straight-chain alkylene optionally substituted by 1 to 2 C1-4 alkyl, (3) C2-4 straight-chain alkenylene optionally substituted by 1 to 2 C1-4 alkyl or (4) C2-4 straight-chain alkynylene optionally substituted by 1 to 2 C1-4 alkyl, D is (1) —COOH, (2) —COOR$^2$, (3) tetrazol-5-yl, (4) —CONR$^3$SO$_2$R$^4$, (5) —CH$_2$OH, (6) —CH$_2$OR$^5$, (7) hydroxy, (8) —OR$^5$, (9) formyl, (10) —CONR$^6$R$^7$, (11) —CONR$^8$OR$^9$, (12) —CO—(NH-amino acid residue-CO)$_m$—OH, (13) —O—(CO-amino acid residue-NH)$_m$—H, (14) —OCO—R$^{10}$, (15) —COO—Z$^1$—Z$^2$—Z$^3$ or (16)

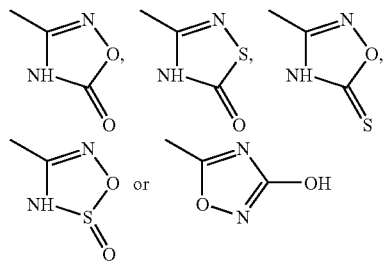

$R^2$ is hydrocarbon which may have a substituent(s), $R^3$ is (1) a hydrogen atom or (2) a hydrocarbon which may have a substituent(s), $R^4$ is a hydrocarbon which may have a substituent(s), $R^5$ is a hydrocarbon which may have a substituent(s), $R^6$ and $R^7$ are each independently (1) a hydrogen atom or (2) a hydrocarbon which may have a substituent(s), $R^8$ and $R^9$ are each independently (1) a hydrogen atom or (2) a hydrocarbon which may have a substituent(s), $R^{10}$ is a hydrocarbon which may have a substituent(s), m is 1 or 2, $Z^1$ is (1) C1-15 alkylene, (2) C2-15 alkenylene, or (3) C2-15 alkynylene, $Z^2$ is (1) —CO—, (2) —OCO—, (3) —COO—, (4) —CONR$^{Z1}$—, (5) —NR$^{Z2}$CO—, (6) —O—, (7) —S—, (8) —SO$_2$—, (9) —SO$_2$—NR$^{Z2}$—, (10) —NR$^{Z2}$SO$_2$—, (11) —NR$^{Z3}$—, (12) —NR$^{Z4}$CONR$^{Z5}$—, (13) —NR$^{Z6}$COO—, (14) —OCONR$^{Z7}$— or (15) —OCOO—, $Z^3$ is (1) a hydrogen atom, (2) C1-15 alkyl, (3) C2-15 alkenyl, (4) C2-15 alkynyl, (5) ring Z or (6) C1-10 alkyl substituted by C1-10 alkoxy, C1-10 alkylthio, C1-10 alkyl-NR$^{Z8}$ or ring Z, ring Z is (1) a cyclic hydrocarbon, or (2) a heterocyclic ring, $R^{Z1}$, $R^{Z2}$, $R^{Z3}$, $R^{Z4}$, $R^{Z5}$, $R^{Z6}$, $R^{Z7}$ and $R^{Z8}$ are each independently a hydrogen atom or C1-15 alkyl, $R^{Z1}$ and $Z^3$ may be taken together with the nitrogen atom to which they are attached to form a 5 to 7 membered nitrogen-containing heterocyclic ring, and the heterocyclic ring may contain other 1 to 3 hetero atom(s) selected from oxygen, nitrogen and sulfur atoms, ring Z and 5 to 7 membered nitrogen-containing heterocyclic ring formed by $R^{Z1}$ and $Z^3$ together with the nitrogen atom to which they are attached may be substituted by 1 to 3 group(s) selected from the following (1) to (4); (1) C1-15 alkyl, (2) C2-15 alkenyl, (3) C2-15 alkynyl, (4) C1-10 alkyl substituted by C1-10 alkoxy, C1-10 alkylthio or C1-10 alkyl-NR$^{Z9}$—;

$R^{Z9}$ is a hydrogen atom or C1-10 alkyl,

E is $E^1$ or $E^2$, $E^1$ is

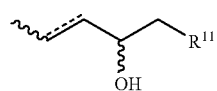

$R^{11}$ is (1) C1-10 alkyl, (2) C1-10 alkylthio, (3) C1-10 alkyl substituted by C3-8 cycloalkyl, (4) C1-10 alkyl substituted by ring 2 or (5) C1-10 alkyl substituted by —W$^1$—W$^2$-ring 2, $W^1$ is (1) —O—, (2) —S—, (3) —SO—, (4) —SO$_2$—, (5) —NR$^{11-1}$—, (6) carbonyl, (7) —NR$^{11-1}$SO$_2$—, (8) carbonylamino or (9) aminocarbonyl, $R^{11-1}$ is (1) a hydrogen atom, (2) C1-10 alkyl or (3) C2-10 acyl, $W^2$ is (1) a bond or (2) C1-8 alkyl optionally substituted by C1-4 alkyl, a halogen atom or hydroxy, $E^2$ is (1) —U$^1$—U$^2$—U$^3$ or (2) ring 4, $U^1$ is (1) C1-4 alkylene, (2) C2-4 alkenylene, (3) C2-4 alkynylene, (4) -ring 3-, (5) C1-4 alkylene-ring 3-, (6) C2-4 alkenylene-ring 3- or (7) C2-4 alkynylene-ring 3-, $U^2$ is (1) a bond, (2) —CH$_2$—, (3) —CHOH—, (4) —O—, (5) —S—, (6) —SO—, (7) —SO$_2$—, (8) —NR$^{12}$—, (9) carbonyl, (10) —NR$^{12}$SO$_2$—, (11) carbonylamino or (12) aminocarbonyl, $R^{12}$ is (1) a hydrogen atom, (2) C1-10 alkyl or (3) C2-10 acyl, $U^3$ is (1) C1-8 alkyl optionally substituted by 1 to 3 substituent(s) selected from C1-10 alkyl, halogen atom, hydroxy, C1-10 alkoxy, C1-10 alkylthio and NR$^{13}$R$^{14}$, (2) C2-8 alkenyl optionally substituted by 1 to 3 substituent(s) selected from C1-10 alkyl, a halogen atom, hydroxy, C1-10 alkoxy, C1-10 alkylthio and NR$^{13}$R$^{14}$, (3) C2-8 alkynyl optionally substituted by 1 to 3 substituent(s) selected from C1-10 alkyl, a halogen atom, hydroxy, C1-10 alkoxy, C1-10 alkylthio and NR$^{13}$R$^{14}$, (4) C1-8 alkyl substituted by ring 4 or (5) ring 4, $R^{13}$ and $R^{14}$ are each independently (1) a hydrogen atom or (2) C1-10 alkyl, ring 1, ring 2, ring 3 and ring 4 are each independently optionally substituted by 1 to 5 R, R is (1) C1-10 alkyl, (2) C2-10 alkenyl, (3) C2-10 alkynyl, (4) C1-10 alkoxy, (5) C1-10 alkylthio, (6) halogen atom, (7) hydroxy, (8) nitro, (9) —NR$^{15}$R$^{16}$, (10) C1-10 alkyl substituted by C1-10 alkoxy, (11) C1-10 alkyl substituted by 1 to 3 halogen atom(s), (12) C1-10 alkyl substituted by C1-10 alkoxy substituted by 1 to 3 halogen atom(s), (13) C1-10 alkyl substituted by —NR$^{15}$R$^{16}$, (14) ring 5, (15) —O-ring 5, (16) C1-10 alkyl substituted by ring 5, (17) C2-10 alkenyl substituted by ring 5, (18) C2-10 alkynyl substituted by ring 5, (19) C1-10 alkoxy substituted by ring 5, (20) C1-10 alkyl substituted by —O-ring 5, (21) —COOR$^{17}$, (22) C1-10 alkoxy substituted by 1 to 4 halogen atom(s), (23) formyl, (24) C1-10 alkyl substituted by hydroxy or (25) C2-10 acyl, $R^{15}$, $R^{16}$ and $R^{17}$ are each independently (1) hydrogen atom or (2) C1-10 alkyl, ring 5 may be substituted by 1 to 3 substituent(s) selected from the following (1) to (9); (1) C1-10 alkyl, (2) C2-10 alkenyl, (3) C2-10 alkynyl, (4) C1-10 alkoxy, (5) C1-10 alkyl substituted by C1-10 alkoxy, (6) halogen atom, (7) hydroxy, (8) C1-10 alkyl substituted by 1 to 3 halogen atom(s), (9) C1-10 alkyl substituted by C1-10 alkoxy substituted by 1 to 3 halogen atom(s);

ring 1, ring 2, ring 3, ring 4 and ring 5 are each independently (1) cyclic hydrocarbon or (2) heterocyclic ring,

 is a single or double bond,

 is α-configuration, β-configuration or a mixture thereof, a salt thereof, a solvate thereof or a cyclodextrin clathrate thereof;

6. The pharmaceutical composition according to above 5, wherein the compound represented by formula (I) is a compound represented by formula (I-A):

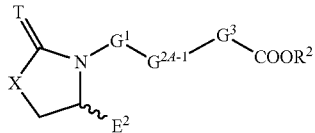

(I-A)

wherein $G^{2A-1}$ is —$Y^a$-ring 1-, $Y^a$ is —S—, —SO$_2$—, —O— or —NR$^1$—, the other symbols have the same meanings as described in above 5;

7. The pharmaceutical composition according to above 5, wherein R$^2$ is C7-20 aliphatic hydrocarbon which may have a substituent(s);

8. The pharmaceutical composition according to above 5, wherein the compound represented by formula (I) is a compound represented by formula (I-1):

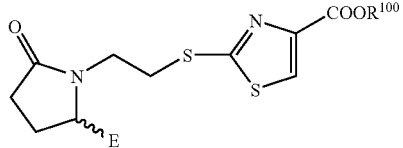

(I-1)

wherein R$^{100}$ is a hydrocarbon which may have a substituent(s), the other symbols have the same meanings as described in above 5;

9. The pharmaceutical composition according to above 8, wherein R$^{100}$ is an aliphatic hydrocarbon having 3 to 22 carbon atoms in its main chain which may have a substituent(s);

10. The pharmaceutical composition according to above 5, wherein the compound represented by formula (I) is 2-[(2-{(2R)-2-[(2-chloro-4-heptylphenoxy)methyl]-5-oxo-1-pyrrolidinyl}ethyl)sulfanyl]-1,3-thiazole-4-carboxylic acid, undecyl 2-[(2-{(2R)-2-[(3,5-dichlorophenoxy)methyl]-5-oxo-1-pyrrolidinyl}ethyl)sulfanyl]-1,3-thiazole-4-carboxylate, 10-phenyldecyl 2-[(2-{(2R)-2-[(3,5-dichlorophenoxy)methyl]-5-oxo-1-pyrrolidinyl}ethyl)sulfanyl]-1,3-thiazole-4-carboxylate, 10-phenyldecyl 2-{[2-((5R)-2-oxo-5-{[3-(trifluoromethoxy)phenoxy]methyl}-1-pyrrolidinyl)ethyl]sulfanyl}-1,3-thiazole-4-carboxylate, undecyl 2-[(2-{(2R)-2-[(heptylamino)methyl]-5-oxo-1-pyrrolidinyl}ethyl)sulfanyl]-1,3-thiazole-4-carboxylate, 10-phenyldecyl 2-[(2-{(2R)-2-[(heptylamino)methyl]-5-oxo-1-pyrrolidinyl}ethyl)sulfanyl]-1,3-thiazole-4-carboxylate or 10-phenyldecyl 2-[(2-{(2R)-2-[(1E)-1-nonenyl]-5-oxo-1-pyrrolidinyl}ethyl)sulfanyl]-1,3-thiazole-4-carboxylate;

11. The pharmaceutical composition according to above 1, which is an agent for preventing and/or treating respiratory disease;

12. The pharmaceutical composition according to above 11, wherein the respiratory disease is asthma, pulmonary injury, pulmonary fibrosis, pulmonary emphysema, bronchitis, chronic obstructive pulmonary disease, adult respiratory distress syndrome, cystic fibrosis or pulmonary hypertension;

13. A medicament which comprises a combination of the pharmaceutical composition for inhalation comprising the compound represented by formula (I) according to above 5, a salt thereof, a solvate thereof or a cyclodextrin clathrate thereof, and one or more medicament(s) selected from type 4 phosphodiesterase inhibitor, steroids, β-agonist, leukotriene receptor antagonist, thromboxane synthetase inhibitor, thromboxane A$_2$ receptor antagonist, mediator release inhibitor, anti-histamines, xanthine derivative, anticholinergic drugs, cytokine inhibitor, prostaglandins, forskohlin preparation, elastase inhibitor, metalloprotease inhibitor, expectorant, antibiotics and immunosuppressive;

14. A compound represented by formula (I-1a):

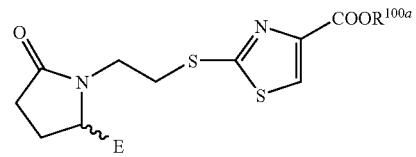

(I-1a)

wherein R$^{100a}$ is hydrocarbon which may have a substituent(s), with the proviso that (1) C1-10 alkyl, (2) phenyl, (3) C1-10 alkyl substituted by phenyl, (4) biphenyl, (5) C1-10 alkyl substituted by biphenyl which may be substituted by 1 to 3 substituent(s) selected from C1-10 alkyl, C1-10 alkoxy, or halogen, and (6) biphenyl which may be substituted by 1 to 3 substituent(s) selected from C1-10 alkyl, C1-10 alkoxy, or halogen are excluded, the other symbols have the same meanings as described in above 5, a salt thereof, a solvate thereof or a cyclodextrin clathrate thereof;

15. The compound according to above 14, wherein R$^{100a}$ is C11-20 alkyl may have a substituent(s), C7-20 alkenyl may have a substituent(s) or C7-20 alkynyl may have a substituent(s), the salt thereof, the solvate thereof or the cyclodextrin clathrate thereof;

16. 2-[(2-{(2R)-2-[(2-chloro-4-heptylphenoxy)methyl]-5-oxo-1-pyrrolidinyl}ethyl)sulfanyl]-1,3-thiazole-4-carboxylic acid, undecyl 2-[(2-{(2R)-2-[(3,5-dichlorophenoxy)methyl]-5-oxo-1-pyrrolidinyl}ethyl)sulfanyl]-1,3-thiazole-4-carboxylate, 10-phenyldecyl 2-[(2-{(2R)-2-[(3,5-dichlorophenoxy)methyl]-5-oxo-1-pyrrolidinyl}ethyl)sulfanyl]-1,3-thiazole-4-carboxylate, 10-phenyldecyl 2-{[2-((5R)-2-oxo-5-{[3-(trifluoromethoxy)phenoxy]methyl}-1-pyrrolidinyl)ethyl]sulfanyl}-1,3-thiazole-4-carboxylate, undecyl 2-[(2-{(2R)-2-[(heptylamino)methyl]-5-oxo-1-pyrrolidinyl}ethyl)sulfanyl]-1,3-thiazole-4-carboxylate, 10-phenyldecyl 2-[(2-{(2R)-2-[(heptylamino)methyl]-5-oxo-1-pyrrolidinyl}ethyl)sulfanyl]-1,3-thiazole-4-carboxylate or 10-phenyldecyl 2-[(2-{(2R)-2-[(1E)-1-nonenyl]-5-oxo-1-pyrrolidinyl}ethyl)sulfanyl]-1,3-thiazole-4-carboxylate, a salt thereof, a solvate thereof or a cyclodextrin clathrate thereof;

17. A method for preventing and/or treating respiratory disease which is characterized by inhalation administration effective dose of a compound represented by formula (I):

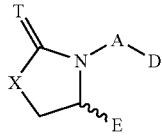

(I)

wherein all symbols have same meanings as described in above 5, a salt thereof, a solvate thereof or a cyclodextrin clathrate thereof;

18. A use of a pharmaceutical composition for inhalation comprising a compound represented by formula (I):

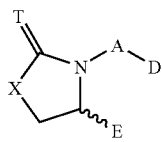

(I)

wherein all symbols have same meanings as described in above 5, a salt thereof, a solvate thereof or a cyclodextrin clathrate thereof for preparing an agent for preventing and/or treating respiratory disease.

Effect of the Invention

A pharmaceutical composition for inhalation comprising a sustained prodrug of EP2 agonist topically exhibits a prolonged bronchodilating and antiinflammatory effects and may avoid any systemic effect such as lowering blood pressure. Therefore, the pharmaceutical composition for inhalation comprising a sustained prodrug of EP2 agonist is useful as a safe agent for preventing and/or treating respiratory diseases (for example, asthma, pulmonary injury (e.g. acute pulmonary injury, chronic pulmonary injury), pulmonary fibrosis, pulmonary emphysema, bronchitis (e.g. acute bronchitis, chronic bronchitis etc.), chronic obstructive pulmonary disease, adult respiratory distress syndrome, cystic fibrosis, pulmonary hypertension or the like).

BEST MODE FOR CARRYING OUT THE INVENTION

As the EP2 agonist reported previously, the compound described in EP860430, ONO-8815Ly, the compound described in JP2000-128858, the compound described in WO99/33794, the compound described in EP974580, the compound described in WO95/19964, the compound described in WO98/28264, the compound described in WO99/19300, the compound described in EP0911321, AH-13205, CP-533536, the compound described in WO98/58911, the compound described in U.S. Pat. No. 5,698,598, the compound described in U.S. Pat. No. 6,376,533, the compound described in WO2004/078103, the compound described in WO2005/012232, the compound described in WO2005/061492, the compound described in WO2005/080367, Butaprost or Rioprostil, Misoprostol and AY23626 are included. These compounds, the salts thereof, the solvates thereof or the prodrugs are preferable as a compound used in the present invention.

Moreover, the EP2 agonist includes not only a compound which has EP2 agonist activity, but also a compound which is converted into EP2 agonist by reaction with enzymes etc. within a living body, namely, a prodrug of EP2 agonist.

As the EP2 agonist to be used in the present invention, a compound in which the bronchodilator effect can be sustained and the hypotensive effect can be reduced is preferred. For example, the duration time of the bronchodilator effect is in the range of from 6 hours to 1 week, preferably from 6 to 48 hours, more preferably from 6 to 24 hours after administration. Furthermore, in the present invention, the reduction of hypotensive effect means that in a dose that allows a bronchodilator effect to be exhibited, a significant decrease in blood pressure is not caused and the rate of change in blood pressure is smaller than with that before administration. The significant decrease in blood pressure refers to a decrease in blood pressure by 20 to 10 mmHg from blood pressure before administration. As for a range of reduction of the hypotensive effect in the present invention, the decrease in blood pressure compared with before drug administration is preferably within 10 mmHg, and more preferably within 5 mmHg.

In the present invention, as the EP2 agonist in which the desired effect in the respiratory organs can be sustained and the hypotensive effect can be reduced, particularly a sustained prodrug of the EP2 agonist is preferred. The sustained prodrug of the EP2 agonist as used herein means a prodrug designed such that an inactive form of the EP2 agonist remains in an affected area in the respiratory organ and is gradually changed into an active form of the EP2 agonist by an enzyme in vivo, and the desired effect can be exhibited in the desired organ in a sustained manner for a long period of time. Since the sustained prodrug of the present invention is gradually changed into an active form of the EP2 agonist in the desired organ, the concentration of the active form of EP2 agonist in the blood does not increase transiently and the hypotensive effect is less likely to be caused.

In the present invention, a carboxylic acid prodrug is preferred as a sustained prodrug of EP2 agonist. The carboxylic acid prodrug means EP2 agonist whose the carboxy is esterified or amidated. As the sustained prodrug of EP2 agonist, a ester of a long-chain aliphatic alcohol or a amide of a long-chain aliphatic amine are preferred particularly.

In the specification, the "ester of a long-chain aliphatic alcohol" is a compound whose carboxy group is esterified with an alcohol having 3 to 22 carbon atoms in its main chain. The number of carbon atoms in the "alcohol having 3 to 22 carbon atoms in its main chain" is preferably 6 to 20, and more preferably 10 to 20. As the ester of a long-chain aliphatic alcohol, for example, decyl ester, 10-phenyldecyl ester or undecyl ester etc. is preferred. The "long-chain aliphatic alcohol" may be substituted by a substituent(s). The "substituent" has the same meaning as substituent of $R^2$ described below. Preferably, for example, phenyl or hydroxy is included.

In the specification, the "amide of a long-chain aliphatic amine" is a compound whose carboxy group is amidated with an amine substituted by aliphatic hydrocarbon having 3 to 22 carbon atoms in its main chain. The number of carbon atoms in the "amine substituted by aliphatic hydrocarbon having 3 to 22 carbon atoms in its main chain" is preferably 6 to 20, and more preferably 10 to 20. As the aliphatic hydrocarbon having 3 to 22 carbon atoms in its main chain, for example, C3-22 alkyl, C3-22 alkenyl or C3-22 alkynyl is included.

C3-22 alkyl is propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, icosyl, henicosanyl, docosanyl or isomer thereof.

C3-22 alkenyl is propenyl, butenyl, pentenyl, hexenyl, heptenyl, octenyl, nonenyl, decenyl, undecenyl, dodecenyl, tridecenyl, tetradecenyl, pentadecenyl, hexadecenyl, heptadecenyl, octadecenyl, nonadecenyl, icosenyl, henicosenyl, docosenyl, butadienyl, pentadienyl, hexadienyl, heptadienyl, octadienyl, nonadienyl, decadienyl, undecadienyl, dodecadienyl, tridecadienyl, tetradecadienyl, pentadecadienyl, hexadecadienyl, heptadecadienyl, octadecadienyl, nonadecadienyl, icosadienyl, henicosadienyl, docosadienyl, hexatrienyl, heptatrienyl, octatrienyl, nonatrienyl, decatrienyl, undecatrienyl, dodecatrienyl, tridecatrienyl, tetradecatrienyl, pentadecatrienyl, hexadecatrienyl, heptadecatrienyl, octadecatrienyl, nonadecatrienyl, icosatrienyl, henicosatrienyl, docosatrienyl or isomer thereof.

C3-22 alkynyl is propynyl, butynyl, pentynyl, hexynyl, heptynyl, octynyl, nonynyl, decynyl, undecynyl, dodecynyl, tridecynyl, tetradecynyl, pentadecynyl, hexadecynyl, heptadecynyl, octadecynyl, nonadecynyl, icosynyl, henicosynyl, docosynyl, butadiynyl, pentadiynyl, hexadiynyl, heptadiynyl, octadiynyl, nonadiynyl, decadiynyl, undecadiynyl, dodecadiynyl, tridecadiynyl, tetradecadiynyl, pentadecadiynyl, hexadecadiynyl, heptadecadiynyl, octadecadiynyl, nonadecadiynyl, icosadiynyl, henicosadiynyl, docosadiynyl, hexatriynyl, heptatriynyl, octatriynyl, nonatriynyl, decatriynyl, undecatriynyl, dodecatriynyl, tridecatriynyl, tetradecatriynyl, pentadecatriynyl, hexadecatriynyl, heptadecatriynyl, octadecatriynyl, nonadecatriynyl, icosatriynyl, henicosatriynyl, docosatriynyl or isomer thereof.

Preferably the long-chain aliphatic amine is, for example, decylamine, undecylamine etc. The long-chain aliphatic amine may be substituted by a substituent(s). The "substituent" has the same mean as substituent of $R^2$ described below. Preferably, for example, phenyl or hydroxy is included.

As the sustained prodrug of EP2 agonist, concretely, undecyl 2-[(2-{(2R)-2-[(3,5-dichlorophenoxy)methyl]-5-oxo-1-pyrrolidinyl}ethyl)sulfanyl]-1,3-thiazole-4-carboxylate, 10-phenyldecyl 2-[(2-{(2R)-2-[(3,5-dichlorophenoxy)methyl]-5-oxo-1-pyrrolidinyl}ethyl)sulfanyl]-1,3-thiazole-4-carboxylate, 10-phenyldecyl 2-{[2-((5R)-2-oxo-5-{[3-(trifluoromethoxy)phenoxy]methyl}-1-pyrrolidinyl)ethyl]sulfanyl}-1,3-thiazole-4-carboxylate, undecyl 2-[(2-{(2R)-2-[(heptylamino)methyl]-5-oxo-1-pyrrolidinyl}ethyl)sulfanyl]-1,3-thiazole-4-carboxylate, 10-phenyldecyl 2-[(2-{(2R)-2-[(heptylamino)methyl]-5-oxo-1-pyrrolidinyl}ethyl)sulfanyl]-1,3-thiazole-4-carboxylate or 10-phenyldecyl 2-[(2-{(2R)-2-[(1E)-1-nonenyl]-5-oxo-1-pyrrolidinyl}ethyl)sulfanyl]-1,3-thiazole-4-carboxylate, a salt thereof, a solvate thereof or a cyclodextrin clathrate thereof is preferable.

As EP2 agonist, for example, a compound represented by formula (I):

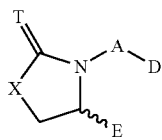

(I)

wherein all symbols have the same meanings as described above, is included.

In the specification, C1-4 alkyl is methyl, ethyl, propyl, butyl or isomer thereof.

In the specification, C1-8 alkyl is methyl, ethyl, propyl, butyl, pentyl, hexyl, heptyl, octyl or isomer thereof.

In the specification, C1-10 alkyl is methyl, ethyl, propyl, butyl, pentyl, hexyl, heptyl, octyl, nonyl, decyl or isomer thereof.

In the specification, C1-15 alkyl is methyl, ethyl, propyl, butyl, pentyl, hexyl, heptyl, octyl, nonyl, decyl, undecyl, dodecyl, tridecyl, tetradecyl, pentadecyl or isomer thereof.

In the specification, C1-20 alkyl is methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, icosyl or isomer thereof.

In the specification, C7-20 alkyl is heptyl, octyl, nonyl, decyl, undecyl, dodecyl, tridecyl, tetradecyl, pentadecyl, hexadecyl, heptadecyl, octadecyl, nonadecyl, icosyl or isomer thereof.

In the specification, C11-20 alkyl is undecyl, dodecyl, tridecyl, tetradecyl, pentadecyl, hexadecyl, heptadecyl, octadecyl, nonadecyl, icosyl or isomer thereof.

In the specification, C2-8 alkenyl is ethenyl, propenyl, butenyl, pentenyl, hexenyl, heptenyl, octenyl or isomer thereof.

In the specification, C2-10 alkenyl is ethenyl, propenyl, butenyl, pentenyl, hexenyl, heptenyl, octenyl, nonenyl, decenyl or isomer thereof.

In the specification, C2-15 alkenyl is vinyl, propenyl, butenyl, pentenyl, hexenyl, heptenyl, octenyl, nonenyl, decenyl, undecenyl, dodecenyl, tridecenyl, tetradecenyl, pentadecenyl, butadienyl, pentadienyl, hexadienyl, heptadienyl, octadienyl, nonadienyl, decadienyl, undecadienyl, dodecadienyl, tridecadienyl, tetradecadienyl, pentadecadienyl, hexatrienyl, heptatrienyl, octatrienyl, nonatrienyl, decatrienyl, undecatrienyl, dodecatrienyl, tridecatrienyl, tetradecatrienyl, pentadecatrienyl or isomer thereof.

In the specification, C2-20 alkenyl is vinyl, propenyl, butenyl, pentenyl, hexenyl, heptenyl, octenyl, nonenyl, decenyl, undecenyl, dodecenyl, tridecenyl, tetradecenyl, pentadecenyl, hexadecenyl, heptadecenyl, octadecenyl, nonadecenyl, icosenyl, butadienyl, pentadienyl, hexadienyl, heptadienyl, octadienyl, nonadienyl, decadienyl, undecadienyl, dodecadienyl, tridecadienyl, tetradecadienyl, pentadecadienyl, hexadecadienyl, heptadecadienyl, octadecadienyl, nonadecadienyl, icosadienyl, hexatrienyl, heptatrienyl, octatrienyl, nonatrienyl, decatrienyl, undecatrienyl, dodecatrienyl, tridecatrienyl, tetradecatrienyl, pentadecatrienyl, hexadecatrienyl, heptadecatrienyl, actadecatrienyl, nonadecatrienyl, icosatrienyl or isomer thereof.

In the specification, C7-20 alkenyl is heptenyl, octenyl, nonenyl, decenyl, undecenyl, dodecenyl, tridecenyl, tetradecenyl, pentadecenyl, hexadecenyl, heptadecenyl, octadecenyl, nonadecenyl, icosenyl, heptadienyl, octadienyl, nonadienyl, decadienyl, undecadienyl, dodecadienyl, tridecadienyl, tetradecadienyl, pentadecadienyl, hexadecadienyl, heptadecadienyl, octadecadienyl, nonadecadienyl, icosadienyl, heptatrienyl, octatrienyl, nonatrienyl, decatrienyl, undecatrienyl, dodecatrienyl, tridecatrienyl, tetradecatrienyl, pentadecatrienyl, hexadecatrienyl, heptadecatrienyl, octadecatrienyl, nonadecatrienyl, icosatrienyl or isomer thereof.

In the specification, C2-8 alkynyl is ethynyl, propynyl, butynyl, pentynyl, hexynyl, heptynyl, octynyl or isomer thereof.

In the specification, C2-10 alkynyl is ethynyl, propynyl, butynyl, pentynyl, hexynyl, heptynyl, octynyl, nonynyl, decynyl or isomer thereof.

In the specification, C2-15 alkynyl is ethynyl, propynyl, butynyl, pentynyl, hexynyl, heptynyl, octynyl, nonynyl, decynyl, undecynyl, dodecynyl, tridecynyl, tetradecynyl, pentadecynyl, butadiynyl, pentadiynyl, hexadiynyl, heptadiynyl, octadiynyl, nonadiynyl, decadiynyl, undecadiynyl, dodecadiynyl, tridecadiynyl, tetradecadiynyl, pentadecadiynyl, hexatriynyl, heptatriynyl, actatriynyl, nonatriynyl, decatriynyl, undecatriynyl, dodecatriynyl, tridecatriynyl, tetradecatriynyl, pentadecatriynyl or isomer thereof.

In the specification, C2-20 alkynyl is ethynyl, propynyl, butynyl, pentynyl, hexynyl, heptynyl, octynyl, nonynyl, decynyl, undecynyl, dodecynyl, tridecynyl, tetradecynyl, pentadecynyl, hexadecynyl, heptadecynyl, octadecynyl, nonadecynyl, icosynyl, butadiynyl, pentadiynyl, hexadiynyl, heptadiynyl, octadiynyl, nonadiynyl, decadiynyl, undecadiynyl, dodecadiynyl, tridecadiynyl, tetradecadiynyl, pentadecadiynyl, hexadecadiynyl, heptadecadiynyl, octadecadiynyl, nonadecadiynyl, icosadiynyl, hexatriynyl, heptatriynyl, octatriynyl, nonatriynyl, decatriynyl, undecatriynyl, dodecatriynyl, tridecatriynyl, tetradecatriynyl, pentadecatriynyl, hexadecatriynyl, heptadecatriynyl, octadecatriynyl, nonadecatriynyl, icosatriynyl or isomer thereof.

In the specification, C7-20 alkynyl is heptynyl, octynyl, nonynyl, decynyl, undecynyl, dodecynyl, tridecynyl, tetradecynyl, pentadecynyl, hexadecynyl, heptadecynyl, octadecynyl, nonadecynyl, icosynyl, heptadiynyl, octadiynyl, nonadiynyl, decadiynyl, undecadiynyl, dodecadiynyl, tridecadiynyl, tetradecadiynyl, pentadecadiynyl, hexadecadiynyl, heptadecadiynyl, octadecadiynyl, nonadecadiynyl, icosadiynyl, heptatriynyl, octatriynyl, nonatriynyl, decatriynyl, undecatriynyl, dodecatriynyl, tridecatriynyl, tetradecatriynyl, pentadecatriynyl, hexadecatriynyl, heptadecatriynyl, octadecatriynyl, nonadecatriynyl, icosatriynyl or isomer thereof.

In the specification, C1-4 straight-chain alkylene is methylene, ethylene, trimethylene or tetramethylene.

In the specification, C2-8 straight-chain alkylene is ethylene, trimethylene, tetramethylene, pentamethylene, hexamethylene, heptamethylene and octamethylene.

In the specification, C1-4 alkylene is methylene, ethylene, trimethylene, tetramethylene or isomer thereof.

In the specification, C1-15 alkylene is methylene, ethylene, trimethylene, tetramethylene, pentamethylene, hexamethylene, heptamethylene, octamethylene, nonamethylene, decamethylene, undecamethylene, dodecamethylene, tridecamethylene, tetradecamethylene, pentadecamethylene or isomer thereof.

In the specification, C2-4 straight-chain alkenylene is ethenylene, propenylene and butenylene.

In the specification, C2-8 straight-chain alkenylene, which has one or two double bond, is ethenylene, propenylene, butenylene, butadienylene, pentenylene, pentadienylene, hexenylene, hexadienylene, heptenylene, heptadienylene, octenylene and octadienylene.

In the specification, C2-4 alkenylene is ethenylene, propenylene, butenylene or isomer thereof.

In the specification, C2-15 alkenylene is ethenylene, propenylene, butenylene, pentenylene, hexenylene, heptenylene, octenylene, nonenylene, decenylene, undecenylene, dodecenylene, tridecenylene, tetradecenylene, pentadecenylene or isomer thereof.

In the specification, C2-4 straight-chain alkynylene is ethynylene, propynylene or butynylene.

In the specification, C2-8 straight-chain alkynylene, which has one or two triple bond, is ethynylene, propynylene, butynylene, butadiynylene, pentynylene, pentadiynylene, hexynylene, hexadiynylene, heptynylene, heptadiynylene, octynylene and octadiynylene.

In the specification, C2-4 alkynylene is ethynylene, propynylene, butynylene or isomer thereof.

In the specification, C2-15 alkynylene is ethynylene, propynylene, butynylene, pentynylene, hexynylene, heptynylene, octynylene, nonynylene, decynylene, undecynylene, dodecynylene, tridecynylene, tetradecynylene, pentadecynylene or isomer thereof.

In the specification, C1-10 alkoxy is methoxy, ethoxy, propoxy, butoxy, pentyloxy, hexyloxy, heptyloxy, octyloxy, nonyloxy, decyloxy or isomer thereof.

In the specification, C1-10 alkylthio is methylthio, ethylthio, propylthio, butylthio, pentylthio, hexylthio, heptylthio, octylthio, nonylthio, decylthio or isomer thereof.

In the specification, C3-8 cycloalkyl is cyclopropyl, cyclobutyl, cyclopentyl, cyclohexyl, cycloheptyl or cyclooctyl.

In the specification, C2-10 acyl is ethanoyl, propanoyl, butanoyl, pentanoyl, hexanoyl, heptanoyl, octanoyl, nonanoyl, decanoyl or isomer thereof.

In formula (I), halogen atom is fluorine, chlorine, bromine or iodine.

In the specification, amino acid of —CO—(NH-amino acid residue-CO)$_m$—OH and —O—(CO-amino acid residue-NH)$_m$—H, which means natural amino acid or abnormal amino acid, includes, for example, glycine, alanine, valine, leucine, isoleucine, serine, threonine, cystein, methionine, proline, asparagine, glutamine, phenylalanine, tyrosine, tryptophan, aspartic acid, glutamic acid, lysine, arginine, histidine, β-alanine, cystathionine, cystine, homoserine, isoleucine, lanthionine, norleucine, norvaline, ornithine, sarcosine, thyronine etc.

In amino acid residue in —CO—(NH— amino acid residue-CO)$_m$—OH and —O—(CO-amino acid residue-NH)$_m$—H, an amino acid with protecting group is included.

In the specification, the "cyclic hydrocarbon" represented by ring 1, ring 2, ring 3, ring 4, ring 5 or ring Z is included an "unsaturated cyclic hydrocarbon" or a "saturated cyclic hydrocarbon". The "saturated cyclic hydrocarbon" is a "3-15 membered saturated cyclic hydrocarbon" which is cycloalkane such as cyclopropane, cyclobutane, cyclopentane, cyclohexane, cycloheptane, cyclooctane, cyclononane, cyclodecane, cycloundecane, cyclododecane, cyclotridecan, cyclotetradecane or cyclopentadecane, perhydropentalene, perhydroazulene, perhydroindene, perhydronaphthalene, perhydroheptalene, spiro[4.4]nonane, spiro[4.5]decane, spiro[5.5]undecane, bicyclo[2.2.1]heptane, bicyclo[3.1.1]heptane, bicyclo[2.2.2]octane, adamantane or noradamantane etc. The "unsaturated cyclic hydrocarbon" is included a "3-15 membered unsaturated cyclic hydrocarbon" which is cycloalkene such as cyclopentene, cyclohexene, cycloheptene, cyclooctene, cyclopentadiene, cyclohexadiene, cycloheptadiene or cyclooctadiene, aromatic hydrocarbon such as benzene, azulene, naphthalene, phenanthrene, anthracene or biphenyl (for example, 2-phenylphenyl, 3-phenylphenyl and 4-phenylphenyl etc.), pentalene, inden, indan, dihydronaphthalene, teterahydronaphthalene, heptalene, biphenylene, as-indacene, s-indacene, acenaphthene, acenaphthylene, fluorene, phenalene, bicyclo[2.2.1]hept-2-ene, bicyclo[3.1.1]hept-2-ene or bicyclo[2.2.2]oct-2-ene etc.

In the specification, the "heterocyclic ring" represented by ring 1, ring 2, ring 3, ring 4, ring 5 or ring Z is mono-, bi- or tri-heterocyclic ring which may have 1 to 7 hetero atom(s) selected from nitrogen atom, oxygen atom and sulfur atom. The "heterocyclic ring" includes, for example, a "3 to 15 membered mono-, bi- or tri-unsaturated heterocyclic ring" or a "3 to 15 membered mono-, bi- or tri-saturated heterocyclic ring" etc.

The "3 to 15 membered mono-, bi- or tri-unsaturated heterocyclic ring" includes, for example, mono-aromatic heterocyclic ring such as pyrrole, imidazole, triazole, tetrazole, pyrazole, pyridine, pyrazine, pyrimidine, pyridazine, triazine, furan, thiophene, oxazole, isoxazole, thiazole, isothiazole, furazan, oxadiazole or thiadiazole, condensed aromatic heterocyclic ring such as indole, isoindole, benzofuran, isobenzofuran, benzothiophene, isobenzothiophene, indazole, quinoline, isoquinoline, purine, phthalazine, pteridine, naphthyridine, quinoxaline, quinazoline, cinnoline, benzoxazole, benzothiazole, benzimidazole, benzofurazan, benzothiadiazole, benzotriazole, carbazole, β-carboline, acridine, phenazine, dibenzofuran, dibenzothiophene, phenanthridine, phenanthroline or perimidine, fused non-aromatic heterocyclic ring such as azepine, diazepine, pyran, oxepine, thiopyran, thiepine, oxazine, oxadiazine, oxazepine, oxadiazepine, thiazine, thiadiazine, thiazepine, thiadiazepine, indolizine, dithianaphthalene, quinolizine, chromene, benzoxepine, benzoxazepine, benzoxadiazepine, benzothiepine, benzothiazepine, benzothiadiazepine, benzazepine, benzodiazepine, xanthene, phenothiazine, phenoxazine, phenoxathiin, thianthrene, pyrroline, imidazoline, triazoline, tetrazoline, pyrazoline, dihydropyridine, tetrahydropyridine, dihydropyrazine, tetrahydropyrazine, dihydropyrimidine, tetrahydropyrimidine, dihydropyridazine, tetrahydropyridazine, tetrahydrotriazine, dihydroazepine, tetrahydroazepine, dihydrodiazepine, tetrahydrodiazepine, dihydrofuran, dihydropyran, dihydrooxepine, tetrahydrooxepine, dihydrothiophene, dihydrothiopyran, dihydrothiepine, tetrahydrothiepine, dihydrooxazole, dihydroisoxazole, dihydrothiazole, dihydroisothiazole, dihydrofurazan, dihydrooxadiazole, dihydrooxazine, dihydrooxadiazine, dihydrooxazepine, tetrahydrooxazepine, dihydrooxadiazepine, tetrahydrooxadiazepine, dihydrothiadiazole, dihydrothiazine, dihydrothiadiazine, dihydrothiazepine, tetrahydrothiazepine, dihydrothiadiazepine, tetrahydrothiadiazepine, indoline, isoindoline, dihydrobenzofuran, dihydroisobenzofuran, dihydrobenzothiophene, dihydroisobenzothiophene, dihydroindazole, dihydroquinoline, tetrahydroquinoline, dihydroisoquinoline, tetrahydroisoquinoline, dihydrophthalazine, tetrahydrophthalazine, dihydronaphthyridine, tetrahydronaphthyridine, dihydroquinoxaline, tetrahydroquinoxaline, dihydroquinazoline, tetrahydroquinazoline, dihydrocinnoline, tetrahydrocinnoline, benzoxathiane, dihydrobenzoxazine, dihydrobenzothiazine, pyrazinomorpholine, dihydrobenzoxazole, dihydrobenzothiazole, dihydrobenzimidazole, dihydrobenzazepine, tetrahydrobenzazepine, dihydrobenzodiazepine, benzodioxepane, dihydrobenzoxazepine, tetrahydrobenzoxazepine, dihydrocarbazole, tetrahydrocarbazole, dihydro-β-carboline, tetrahydro-β-carboline, dihydroacridine, tetrahydroacridine, dihydrodibenzofuran, dihydrodibenzothiophene, tetrahydrodibenzofuran, tetrahydrodibenzothiophene, dioxaindan, benzodioxane, chroman, benzodithiolane, benzodithiane, 6,7,8,9-tetrahydro-5H-pyrido[4',3':4,5]pyrrolo[2,3-b]pyridine, 2,3,4,5-tetrahydro-1H-pyrido[4,3-b]indole or 6,7,8,9-tetrahydro-5H-pyrido[3',4':4,5]pyrrolo[2,3-b]pyridine etc. The "3 to 15 membered mono-, bi- or tri-saturated heterocyclic ring" includes, for example, aziridine, azetidine, pyrrolidine, imidazolidine, triazolidine, tetrazolidine, pyrazolidine, piperidine, piperazine, perhydropyrimidine, perhydropyridazine, perhydroazepine, perhydrodiazepine, perhydroazocine, oxirane, oxetane, tetrahydrofuran, tetrahydropyran, perhydrooxepine, thiirane, thietane, tetrahydrothiophene, tetrahydrothiopyran, perhydrothiepine, tetrahydrooxazole (oxazolidine), tetrahydroisoxazole (isoxazolidine), tetrahydrothiazole (thiazolidine), tetrahydroisothiazole (isothiazolidine), tetrahydrofurazan, tetrahydrooxadiazole (oxadiazolidine), tetrahydrooxazine, tetrahydrooxadiazine, perhydrooxazepine, perhydrooxadiazepine, tetrahydrothiadiazole (thiadiazolidine), tetrahydrothiazine, tetrahydrothiadiazine, perhydrothiazepine, perhydrothiadiazepine, morpholine, thiomorpholine, oxathiane, perhydrobenzofuran, perhydroisobenzofuran, perhydrobenzothiophene, perhydroisobenzothiophene, perhydroindazole, perhydroquinoline, perhydroisoquinoline, perhydrophthalazine, perhydronaphthyridine, perhydroquinoxaline, perhydroquinazoline, perhydrocinnoline, perhydrobenzoxazole, perhydrobenzothiazole, perhydrobenzimidazole, perhydrocarbazole, perhydro-β-carboline, perhydroacridine, perhydrodibenzofuran, perhydrodibenzothiophene, dioxolane, dioxane, dithiolane, dithiane etc.

In the specification, the "5 to 7 membered nitrogen-containing heterocyclic ring" is 5 to 7 membered heterocyclic ring which contains at least one nitrogen atom in addition to carbon atom and may be contain 1 to 3 hetero atom(s) selected from oxygen atom, nitrogen atom and sulfur atom. For example, a "5 to 7 membered nitrogen-containing unsaturated heterocyclic ring" or a "5 to 7 membered nitrogen-containing saturated heterocyclic ring" is included. Concretely, the "5 to 7 membered nitrogen-containing unsaturated heterocyclic ring" includes, for example, pyrrole, imidazole, triazole, tetrazole, pyrazole, pyrroline, azepine, imidazoline, triazoline, tetrazoline, pyrazoline, dihydropyridine, tetrahydropyridine, dihydropyrazine, tetrahydropyrazine, dihydropyrimidine, tetrahydropyrimidine, dihydropyridazine, tetrahydropyridazine, dihydroazepine, tetrahydroazepine, dihydrodiazepine, tetrahydrodiazepine, dihydrooxazole, dihydroisoxazole, dihydrothiazole, dihydroisothiazole, dihydrofurazan, dihydrooxadiazole, dihydrooxazine, dihydrooxadiazine, dihydrooxazepine, tetrahydrooxazepine, dihydrooxadiazepine, tetrahydrooxadiazepine, dihydrothiadiazole, dihydrothiazine, dihydrothiadiazine, dihydrothiazepine, tetrahydrothiazepine, dihydrothiadiazepine, tetrahydrothiadiazepine etc. The 5-7 membered nitrogen-containing saturated heterocyclic ring" includes pyrrolidine, imidazolidine, triazolidine, tetrazolidine, pyrazolidine, piperidine, piperazine, perhydropyrimidine, perhydropyridazine, perhydroazepine, perhydrodiazepine, tetrahydrooxazole (oxazolidine), tetrahydroisoxazole (isoxazolidine), tetrahydrothiazole (thiazolidine), tetrahydroisothiazole (isothiazolidine), tetrahydrofurazan, tetrahydrooxadiazole (oxadiazolidine), tetrahydrooxazine, tetrahydrooxadiazine, perhydrooxazepine, perhydrooxadiazepine, tetrahydrothiadiazole (thiadiazolidine), tetrahydrothiazine, tetrahydrothiadiazine, perhydrothiazepine, perhydrothiadiazepine, morpholine, thiomorpholine etc.

The "hydrocarbon" in "hydrocarbon which may have a substituent(s)" represented by $R^2$ included, for example, straight or branched chain aliphatic hydrocarbon or cyclic hydrocarbon etc.

The "straight or branched chain aliphatic hydrocarbon" is included, for example, a "C1-20 aliphatic hydrocarbon". The "C1-20 aliphatic hydrocarbon" is included, for example, C1-20 alkyl, C2-20 alkenyl, C2-20 alkynyl etc. The "C1-20 alkyl", the "C2-20 alkenyl" and the "C2-20 alkynyl" have the same meanings as defined above.

The "cyclic hydrocarbon" has the same meaning as the "cyclic hydrocarbon" in ring 1, ring 2, ring 3, ring 4, ring 5 or ring Z.

Preferably, the "hydrocarbon" in the "hydrocarbon which may have a substituent(s)" represented by $R^2$ is C7-20 aliphatic hydrocarbon.

The "substituent" in the "hydrocarbon which may have a substituent(s)" represented by $R^2$ includes (1) hydrocarbon which may have a substituent(s) such as C1-10 alkyl, phenyl, amino, C1-10 alkoxy, sulfo, halogen atom, carboxy, cyano, nitro, oxo, thioxo, hydroxy, trifluoromethyl or trifluoromethoxy. As used herein, the "hydrocarbon" has the same meaning as above-described "hydrocarbon". (2) heterocyclic ring may have a substituent(s) such as hydrocarbon (the "hydrocarbon" has the same meaning as above-described "hydrocarbon"), amino, sulfo, halogen atom, carboxy, cyano, nitro, oxo, thioxo, hydroxy, methoxy, trifluoromethyl, trifluoromethoxy or acetyl. As used herein, the "heterocyclic ring" has the same meaning as the "heterocyclic ring" in ring 1, ring 2, ring 3, ring 4, ring 5 or ring Z. (3) amino, (4) C1-6 acylamino such as acetylamino or propionylamino, (5) primary or secondary amino substituted by hydrocarbon (for example, methylamino, ethylamino, propylamino, isopropylamino, butylamino, heptylamino, octylamino, dimethylamino, diethylamino, cyclohexylamino, 1-carbamoyl-2-cyclohexylethylamino, N-butyl-N-cyclohexylmethylamino, phenylamino, 6,6-dimethylbicyclo[3.1.1]heptylmethylamino etc.). As used herein, the "hydrocarbon" has the same meaning as above-described "hydrocarbon" and is optionally substituted halogen atom, oxo, amino, carbamoyl etc. (6) C1-4 alkylsulfonylamino such as methylsulfonylamino or ethylsulfonylamino, (7) phenylsulfonylamino, (8) C1-4 alkylsulfonyl such as methylsulfonyl or ethylsulfonyl, (9) phenylsulfonyl, (10) halogen atom such as fluorine, chlorine, bromine or iodine, (11) carboxy, (12) cyano, (13) nitro, (14) oxo, (15) thioxo, (16) hydroxy, (17) C1-10 alkoxy such as methoxy, ethoxy, propoxy, isopropoxy, butoxy, isobutoxy, sec-butoxy, tert-butoxy, cyclohexylmethyloxy or benzyloxy, (18) C3-8 cycloalkoxy such as cyclohexyloxy, (19) phenoxy which may be substituted by C1-4 alkyl, halogen atom, trifluoromethyl or trifluoromethoxy etc., (20) 5,6,7,8-tetrahydro-1-naphthyloxo, (21) mercapto, (22) C1-4 alkylthio such as methylthio, ethylthio, propylthio, isopropylthio, butylthio or tert-butylthio, (23) phenylthio, (24) carbamoyl, (25) aminocarbonyl which may be substituted by C1-8 hydrocarbon (for example, N-butylaminocarbonyl, N-cyclohexylmethylaminocarbonyl, N-butyl-N-cyclohexylmethylaminocarbonyl, N-cyclohexylaminocarbonyl, phenylaminocarbonyl etc.). As used herein, the "hydrocarbon" has the same meaning as the above-described "hydrocarbon". (26) sulfamoyl, (27) aminosulfonyl substituted by hydrocarbon (for example, methylaminosulfonyl etc.). As used herein, the "hydrocarbon" has the same meaning as above-described "hydrocarbon". (28) aminosulfonyl substituted by hydrocarbon substituted by amino (for example, dimethylaminoethylaminosulfonyl, dimethylaminopropylaminosulfonyl etc.). As used herein, the "hydrocarbon" has the same meaning as above-described "hydrocarbon". (29) C1-6 alkoxycarbonyl such as methoxycarbonyl, ethoxycarbonyl, tert-butoxycarbonyl, (30) sulfo (—SO$_3$H), (31) sulfino, (32) phosphono, (33) amidino, (34) imino, (35) —B(OH)$_2$, (36) C1-4 alkylsulfinyl such as methylsulfinyl or ethylsulfinyl, (37) C1-6 acyl such as formyl, acetyl, propionyl or butylyl, (38) benzoyl, (39) hydroxyimino, (40) C1-8 alkyloxyimino such as methyloxyimino or ethyloxyimino etc. The "hydrocarbon which may have a substituent(s)" may have 1 to 5 substituent(s) selected from above (1) to (49). When the number of substituent is two or more, the substituents are the same or different.

Preferably, the "substituent" in the "hydrocarbon which may have a substituent(s)" represented by $R^2$ is, for example, phenyl or hydroxy etc.

The "substituent" in the "hydrocarbon which may have a substituent(s)" represented by $R^3$, $R^4$, $R^5$, $R^6$, $R^7$, $R^8$, $R^9$ or $R^{10}$ has the same meaning as the "substituent" in the "hydrocarbon which may have a substituent(s)" in $R^2$.

Preferably, A is $A^1$ or $A^2$ in formula (I), more preferably $A^2$.

Preferably, ring 1 is C3-10 cyclic hydrocarbon or 3 to 10 membered heterocyclic ring, more preferably C3-7 cyclic hydrocarbon or 3 to 7 membered heterocyclic ring.

More preferably, ring 1 is C5 or 6 cyclic hydrocarbon or 5 or 6 membered heterocyclic ring, especially furan, thiophene, oxazole or benzene.

Preferably, D is —COOH, —COOR$^2$ or —COO—Z$^1$—Z$^2$—Z$^3$.

Preferably, $R^2$ is C7-20 aliphatic hydrocarbon which may have a substituent(s).

Preferably, $Z^1$ is C1-15 alkylene, more preferably C1-8 alkylene, especially C1-4 alkylene.

Preferably, $Z^2$ is —CO—, —OCO—, —COO—, —CONRZ$^1$, —OCONRZ$^7$, —OCOO—, more preferably —OCO—, —OCONRZ$^7$, —OCOO—.

Preferably, $Z^3$ is C1-15 alkyl, C1-10 alkoxy, C1-10 alkylthio, C1-10 alkyl-NRZ$^8$- or C1-10 alkyl substituted by ring Z, more preferably C4-12 alkyl.

Preferably, T is oxygen atom or sulfur atom in formula (I), more preferably oxygen.

Preferably, X is —CH$_2$—, —O— or —S— in formula (I), more preferably —CH$_2$—.

Preferably, E is $E^2$ in formula (I).

Preferably, $E^2$ is —U$^1$—U$^2$—U$^3$. Preferably, U$^1$ is C1-4 alkylene, C2-4 alkenylene or C2-4 alkynylene. Preferably, U$^2$ is —CHOH—, —O—, —S—, —SO—, —SO$_2$— or —NR$^{12}$—.

Preferably, the compound represented by formula (I) is the compound represented by formula (I-A):

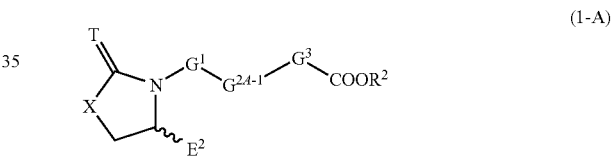

(I-A)

wherein $G^{2A-1}$ is —Y$^a$-ring 1-, Y$^a$ is —S—, —SO$_2$—, —O— or —NR$^1$—, the other symbols have the same meanings as described above.

Preferably, the compound represented by formula (I-A) is the compound represented by formula (I-A-a):

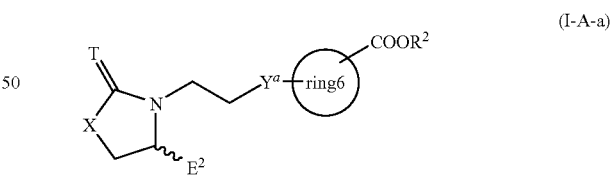

(I-A-a)

wherein ring 6 is C5 or 6 cyclic hydrocarbon or 5 or 6 membered heterocyclic ring, $R^2$ is hydrocarbon which may have a substituent(s), the other symbols have the same meanings as described above.

Preferably, ring 6 is furan, thiophene, oxazole, thiazole or benzene. That is,

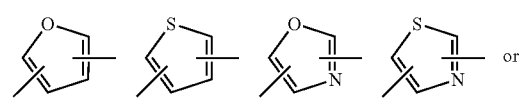

or

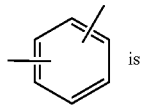

included. Binding site can be anywhere other than same carbon.

More preferably, the compound represented formula (I-A) is the compound represented by formula (I-A-b):

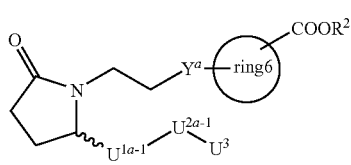

(I-A-b)

wherein $U^{1a-1}$ is C1-4 alkylene, C2-4 alkenylene, C2-4 alkynylene, $U^{2a-1}$ or —CHOH—, —O—, —S—, —SO—, —SO$_2$—, —NR$^{12}$—, the other symbols have the same meanings as described above, the compound represented by formula (I-A-c):

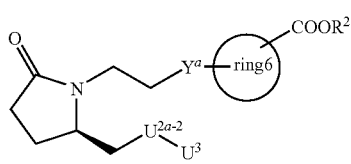

(I-A-c)

wherein $U^{2a-2}$ is —O— or —NR$^{12}$—, the other symbols have the same meanings as described above, or the compound represented by formula (I-A-d):

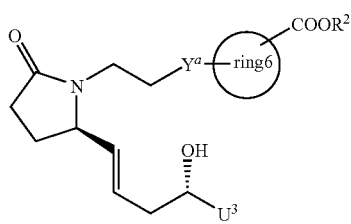

(I-A-d)

wherein all symbols have the same meanings as described above.

Preferably, the compound represented by formula (I) is, for example, the compound represented by

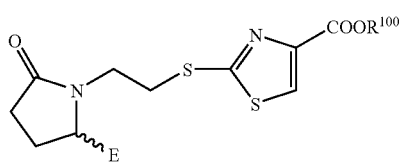

(I-1)

wherein $R^{100}$ is hydrocarbon which may have a substituent(s), the other symbol have the same meanings as described above. The hydrocarbon in the "hydrocarbon which may have a substituent(s)" represented by $R^{100}$ has the same meaning as the "hydrocarbon which may have a substituent(s)" represented by $R^2$. Preferably, $R^{100}$ is hydrocarbon which has 3 to 22 carbon atoms in its main chain and may have a substituent(s), more preferably hydrocarbon which has 6 to 20 carbon atoms in its main chain and may have a substituent (s). Especially, hydrocarbon which has 10 to 20 carbon atoms in its main chain and may have a substituent(s) is preferred. As used herein, the substituent in the "hydrocarbon which may have a substituent(s)" represented by $R^{100}$ has the same meaning as the "hydrocarbon which may have a substituent(s)" represented by $R^2$. Preferably, for example, phenyl or hydroxy etc. is included.

Preferably, the compound used as the pharmaceutical composition for inhalation in the present invention is 2-[(2-{(2R)-2-[(2-chloro-4-heptylphenoxy)methyl]-5-oxo-1-pyrrolidinyl}ethyl)sulfanyl]-1,3-thiazole-4-carboxylic acid, undecyl 2-[(2-{(2R)-2-[(3,5-dichlorophenoxy)methyl]-5-oxo-1-pyrrolidinyl}ethyl)sulfanyl]-1,3-thiazole-4-carboxylate, 10-phenyldecyl 2-[(2-{(2R)-2-[(3,5-dichlorophenoxy)methyl]-5-oxo-1-pyrrolidinyl}ethyl)sulfanyl]-1,3-thiazole-4-carboxylate, 10-phenyldecyl 2-{[2-((5R)-2-oxo-5-{[3-(trifluoromethoxy)phenoxy]methyl}-1-pyrrolidinyl)ethyl]sulfanyl}-1,3-thiazole-4-carboxylate, undecyl 2-[(2-{(2R)-2-[(heptylamino)methyl]-5-oxo-1-pyrrolidinyl}ethyl) sulfanyl]-1,3-thiazole-4-carboxylate, 10-phenyldecyl 2-[(2-{(2R)-2-[(heptylamino)methyl]-5-oxo-1-pyrrolidinyl}ethyl) sulfanyl]-1,3-thiazole-4-carboxylate or 10-phenyldecyl 2-[(2-{(2R)-2-[(1E)-1-nonenyl]-5-oxo-1-pyrrolidinyl}ethyl)sulfanyl]-1,3-thiazole-4-carboxylate etc.

Preferred compounds are all described in Example.

Moreover, for example, 2-[(2-{(2R)-2-[(1E,4S)-4-(1-ethylcyclobutyl)-4-hydroxybut-1-enyl]-5-oxopyrrolidin-1-yl}ethyl)sulfanyl]-1,3-thiazole-4-carboxylic acid, 2-[(2-{(2R)-2-[(3,5-dichlorophenoxy)methyl]-5-oxopyrrolidin-1-yl}ethyl)thio]-1,3-thiazole-4-carboxylic acid, 2-{[2-((2R)-2-{[2-chloro-3-(trifluoromethyl)phenoxy]methyl}-5-oxopyrrolidin-1-yl)ethyl]sulfanyl}-1,3-thiazole-4-carboxylic acid, 2-{[2-((5R)-2-oxo-5-{[3-(trifluoromethoxy)phenoxy]methyl}pyrrolidin-1-yl)ethyl]sulfanyl}-1,3-thiazole-4-carboxylic acid or butyl 2-[(2-{(2R)-2-[(3,5-dichlorophenoxy)methyl]-5-oxopyrrolidin-1-yl}ethyl)thio]-1,3-thiazole-4-carboxylate etc. is preferred.

Meanwhile, the compound represented by formula (I-1a):

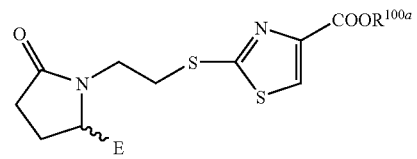

(I-1a)

wherein $R^{100a}$ is hydrocarbon which may have a substituent(s), with the proviso that, (1) C1-10 alkyl, (2) phenyl, (3) C1-10 alkyl substituted by phenyl, (4) biphenyl, (5) C1-10 alkyl substituted by biphenyl which may have 1 to 3 substituent(s) selected from C1-10 alkyl, C1-10 alkoxy or halogen atom and (6) biphenyl substituted by 1 to 3 substituent(s) selected from C1-10 alkyl, C1-10 alkoxy or halogen atom are excluded, the other symbol has the same meaning as described above, is a new compound among the compound represented by formula (I-1) in the present invention. Especially preferred is the compound represented by formula (I-1-a):

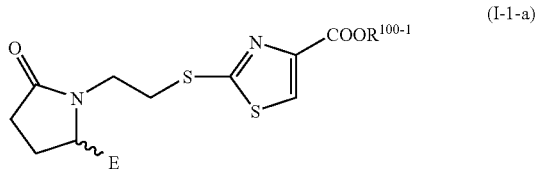

wherein $R^{100-1}$ is C11-20 alkyl which may have a substituent(s), C7-20 alkenyl which may have a substituent(s) or C7-20 alkynyl which may have a substituent(s), the other symbol have the same meanings as described above. The substituent in the "C11-20 alkyl which may have a substituent(s)", "C7-20 alkenyl which may have a substituent(s)" and "C7-20 alkynyl which may have a substituent(s)" represented by $R^{100-1}$ has the same meaning as the substituent in the "hydrocarbon which may have a substituent(s)" represented by above-described $R^2$. For example, phenyl or hydroxy is preferred.

According to the present invention, unless otherwise indicated and as is apparent for those skilled in the art, the symbol ⋯ indicates that it is bound to the opposite side of the sheet (namely α-configuration), the symbol ⁄ indicates that it is bound to the front side of the sheet (namely β-configuration), the symbol ⁄⁄⁄ indicates that it is a α-configuration, β-configuration or a mixture thereof which may be mixed by voluntary ratio, and the symbol ⁄ indicates that it is a mixture of α-configuration and β-configuration which may be mixed by voluntary ratio.

Unless otherwise specified, all isomers are included in the present invention. For example, alkyl, alkenyl, alkynyl, alkoxy, alkylthio, alkylene, alkenylene or alkynylene includes straight-chain or branched-chain ones. In addition, isomers on double bond, ring, fused ring (E-, Z-, cis-, trans-isomer), isomers generated from asymmetric carbon atom(s) (R-, S-isomer, α-, β-configuration, enantiomer, diastereomer), optically active isomers (D-, L-, d-, l-isomer), polar compounds generated by chromatographic separation (more polar compound, less polar compound), equilibrium compounds, rotational isomers, mixtures thereof at voluntary ratios and racemic mixtures are also included in the present invention.

The salt of the compound represented by formula (I) includes pharmacologically acceptable salts etc. Preferably the pharmacologically acceptable salt is a low-toxic and water-soluble one. The suitable salt includes, for example, salts of alkali metals (e.g., potassium, sodium, lithium, etc.), salts of alkaline earth metals (e.g., calcium, magnesium, etc.), ammonium salts (e.g., tetramethylammonium salt, tetrabutylammonium salt, etc.), salts of organic amine (e.g., triethylamine, methylamine, dimethylamine, cyclopentylamine, benzylamine, phenethylamine, piperidine, monoethanolamine, diethanolamine, tris(hydroxymethyl)methylamine, lysine, arginine, N-methyl-D-glucamine, etc.), acid addition salts [salts of inorganic acids (e.g., hydrochloride, hydrobromide, hydroiodide, sulfate, phosphate, nitrate etc.), and salts of organic acids (e.g., acetate, trifluoroacetate, lactate, tartrate, oxalate, fumarate, maleate, benzoate, citrate, methanesulfonate, ethanesulfonate, benzenesulfonate, toluenesulfonate, isethionate, glucuronate, gluconate etc.)].

Moreover, the salt includes a quaternary ammonium salt. The quaternary ammonium salt is the compound represented by formula (I) wherein the nitrogen atom is quarternalized by $R^0$ which is C1-8 alkyl or C1-8 alkyl substituted by phenyl. In the present invention, an N-oxide of the compound represented by formula (I) is included. The N-oxide is the compound wherein nitrogen is oxidized. Moreover the N-oxide may be converted into an alkaline (earth) metal, an ammonium salt, an organic amine salt or an acid addition salt.

As the suitable solvate of the compound represented formula (I), for example, water or alcohol solvents such as ethanol are included. The non-toxic and water-soluble solvate is preferred. Moreover, the solvate of the present invention includes a solvate of an alkaline (earth) metal, an ammonium salt, an organic amine salt, an acid addition salt or an N-oxide of the compound represented by formula (I) described above.

The compound of the present invention may be converted into the salt, the N-oxide or the solvate described above by the known method.

The compounds of represented by formula (I) may be converted into the corresponding cyclodextrin clathrates by the method described in the specification of JP-B-50-3362 corresponding to U.S. Pat. No. 3,816,393, and in the specification of JP-B-52-31404 or 61-52146, the disclosure of each of which is incorporated by reference, using α-, β- or γ-cyclodextrin or a mixture thereof. Converting into the corresponding cyclodextrin clathrates serves to increase the stability and solubility in water of the compounds, and therefore it is useful in the use for pharmaceuticals.

Processes for the Preparation of the Compound in the Present Invention

EP2 agonist used in the present invention can be prepared by the methods by methods which properly improved and combined the methods described in EP860430, JP2000-128858, WO99/33794, EP974580, WO95/19964, WO98/28264, WO99/19300, EP0911321, WO98/58911, U.S. Pat. No. 5,698,598, U.S. Pat. No. 6,376,533, WO2005/061492 or WO2005/080367, the methods based on them or the methods described in Example of the present invention.

The compound represented by formula (I) of the present invention can be prepared by the methods which properly improved and combined known the methods such as the methods described in Comprehensive Organic Transformations: A Guide to Functional Group Preparations, 2nd Edition (Richard C. Larock, John Wiley & Sons Inc, 1999) or WO2003/74483, the methods based on them or the methods described in Example of the present invention.

The compound represented by formula (I-A) can be prepared by esterifying the carboxylic acid derivative of formula (II):

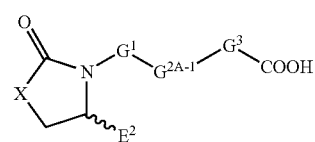

wherein all symbols have the same meanings as described above, and alcohol represented by

 (III)

wherein $R^2$ has the same meaning as described above, as follows.

The esterification is known. For example, it includes (1) dehydration-condensation reaction in the presence of acid catalyst, (2) ester exchange reaction, etc.

(1) Dehydration-Condensation Reaction in the Presence of Acid Catalyst

The compound represented by formula (I) can be prepared, for example, by reaction of the carboxylic acid derivative represented by formula (II) in an organic solvent which is alcohol represented by formula (III) or a mixed solvent of the alcohol and the other organic solvent, in the presence of acid such as an inorganic acid (e.g. sulfuric acid, hydrochloric acid), an organic acid (e.g. p-toluene sulfonic acid, trifluoro acetic acid) or Lewis acid (e.g. trifluoroboran-diethyl ether complex) at 0 to 100° C.

(2) Ester Exchange Reaction

The compound represented by formula (I) can be prepared, for example, by reaction of the simple ester such as methyl ester of the carboxylic acid derivative represented by formula (II) in alcohol solvent represented by formula (III), in the presence of acid such as an inorganic acid (e.g. sulfuric acid, hydrochloric acid), an organic acid (e.g. p-toluene sulfonic acid, trifluoro acetic acid) or Lewis acid (e.g. trifluoroboran-diethyl ether complex), a base such as potassium carbonate, sodium carbonate, cesium carbonate, t-butoxy potassium, sodium methoxide, sodium ethoxide, or titanium alcoxide such as titanium tetraisopropoxide at 0 to 100° C.

In addition to the above esterification, the following esterifications such as (3) the method using an acyl halide, (4) the method using a mixed acid anhydride and (5) the method using a condensing agent may be used.

These methods are explained concretely below.

(3) The method using an acyl halide may be carried out, for example, by reacting carboxylic acid with an acyl halide (e.g. oxalyl chloride or thionyl chloride etc.) in an organic solvent (e.g. chloroform, dichloromethane, diethyl ether or tetrahydrofuran) or without a solvent at −20° C. to reflux temperature, and then the obtained acyl halide derivative may be reacted with alcohol in an organic solvent (e.g. chloroform, dichloromethane, diethyl ether or tetrahydrofuran) in the presence of a base (e.g. pyridine, triethylamine, dimethylaniline, dimethylaminopyridine or diisopropylethylamine etc.) at 0 to 40° C. As an alternative, the obtained acyl halide derivative may be reacted in an organic solvent (e.g. dioxane, tetrahydrofuran) using an alkaline aqueous solution (e.g. sodium bicarbonate, sodium hydroxide) at 0 to 40° C.

(4) The method using a mixed acid anhydride may be carried out, for example, by reacting carboxylic acid with an acyl halide (e.g. pivaloyl chloride, tosyl chloride or mesyl chloride) or an acid derivative (e.g. ethyl chloroformate or isobutyl chloroformate) in an organic solvent (e.g. chloroform, dichloromethane, diethyl ether, tetrahydrofuran) or without a solvent, in the presence of a base (e.g. pyridine, triethylamine, dimethylaniline, dimethylaminopyridine or diisopropylethylamine) at 0 to 40° C., and then the obtained mixed acid anhydride derivative may be reacted with alcohol in an organic solvent (e.g. chloroform, dichloromethane, diethyl ether or tetrahydrofuran), at 0 to 40° C.

(5) The method using a condensing agent may be carried out, for example, by reacting carboxylic acid with alcohol in an organic solvent (e.g. chloroform, dichloromethane, dimethylformamide, diethyl ether or tetrahydrofuran) or without a solvent, in the presence or absence of a base (e.g. pyridine, triethylamine, dimethylaniline or dimethylaminopyridine), using a condensing agent (e.g. 1,3-dicyclohexyl carbodiimide (DCC), 1-ethyl-3-[3-(dimethylamino)propyl]carbodiimide (EDC), 1,1'-carbodiimidazole (CDI), 2-chloro-1-methylpyridinium iodide, or 1-propanephosphonic acid cyclic anhydride (PPA)), in the presence or absence of 1-hydroxybenzothiazole (HOBt) at 0 to 40° C.

The compound represented by formula (I-1) can be prepared by the above esterification of the compound represented by formula (VI):

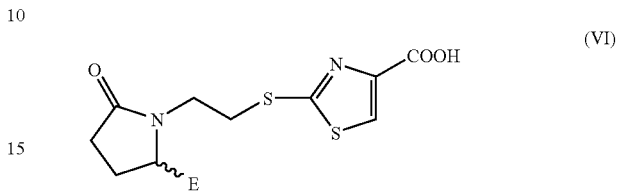

(VI)

wherein all symbols have the same meanings as described above, instead of the compound represented by formula (II) and the compound represented by formula (V):

HO—R$^{100}$ (V)

wherein all symbols have the same meanings as described above, instead of the compound represented by formula (III).

Moreover, the compound represented by formula (I-A) also can be prepared by the following esterification of the carboxylic acid derivative represented by formula (II) and the compound represented by formula (VI):

Q-R$^2$ (VI)

wherein Q is a halogen atom and R$^2$ has the same meaning as described above.

The esterification is known. The compound represented by formula (I) can be prepared, for example, by reacting the carboxylic acid derivative represented by formula (II) and the compound represented by formula (VI) in an organic solvent (e.g. dimethylformamide, dimethylactoeamide dimethylimidazoline, tetrahydrofuran, ethyl eter, ethyl ether, dichloromethane, chloroform) in the presence of a base (e.g. potassium carbonate, sodium carboneta, cesium carbonate, sodium hydride, t-butoxypotassium, sodium methoxide, sodium ethoxide) at 0 to 100° C.

Moreover, the compound represented by formula (I-1) also can be prepared by the above reaction of the compound represented by formula (IV) and the compound represented by formula (VII):

Q-R$^{100}$ (VII)

wherein all symbols have the same meaning as described above.

The above esterification can be carried out either in the presence or absence of the inert gas such as argon or nitrogen.

In the above processes for the preparation, the compound represented by formula (II) or the compound represented by formula (IV) can be prepared by the methods described in WO03/74483 or the modified methods thereof.

The other test compounds is known or can be prepared easily by the combination of the known methods such as the methods described in *Comprehensive Organic Transformations: A Guide to Functional Group Preparations,* 2nd Edition (Richard C. Larock, John Wiley & Sons Inc, 1999) or Elmer J. Rauckman et. al., *J. Org. Chem.*, vol. 41, No. 3, 1976, p 564-565.

In each reaction of the specification, the reactions with heating, as will be apparent to those skilled in the art, it may be carried with water bath, oil bath, sand bath and microwave.

In each reaction of the specification, it may be used a solid phase reagent which is supported by polymer (for example, polystyrene, polyacrylamide, polypropylene or polyethyleneglycol etc.).

In each reaction of the specification, the obtained products may be purified by conventional techniques. For example, the purification may be carried out by distillation at atmospheric or reduced pressure, by high performance liquid chromatography with silica gel or magnesium silicate, by thin layer chromatography, by ion-exchange resin, by scavenger resin, by column chromatography, by washing or by recrystallization. The purification may be done each reaction or after several reactions.

Toxicity

The toxicity of the compound represented by formula (I) is very low and therefore the compound may be considered safe for pharmaceutical use.

Application to Pharmaceuticals

The pharmaceutical composition for inhalation comprising EP2 agonist has bronchodilating and antiinflammatory effects. Therefore, it is useful for preventing and/or treating respiratory diseases such as asthma, pulmonary injury (e.g. acute pulmonary injury, chronic pulmonary injury), pulmonary fibrosis, pulmonary emphysema, bronchitis (e.g. acute bronchitis, chronic bronchitis), chronic obstructive pulmonary disease, adult respiratory distress syndrome, cystic fibrosis or pulmonary hypertension. Moreover, the pharmaceutical composition for inhalation comprising a sustained prodrug of EP2 agonist is a safe and effective agent for preventing and/or treating respiratory diseases in which a desired effect such as a bronchodilating effect is sustained and a hypotensive effect is reduced.

The pharmaceutical composition for inhalation comprising the compound represented by formula (I) may be administered as a combined preparation by combining with other medicaments for the purpose of 1) supplementing and/or enhancing of prevention and/or treatment effect of the compound, 2) improvement in pharmacokinetics and absorption and reduction of dose of the compound, and/or 3) reduction of side effect of the compound.

The compound represented by formula (I) and other medicaments may be administered in the form of combination preparation having these components incorporated in one preparation or may be administered in separate preparations. In the case where these medicaments are administered in separate preparations, they may be administered simultaneously or at different times. In the latter case, the medicament of the present invention may be administered before the other medicaments. Alternatively, the other medicaments may be administered before the medicament of the present invention. The method for the administration of these may be the same or different.

The other medicaments may be low-molecular compounds. In addition, they may be macromolecular protein, polypeptide, polynucleotide (DNA, RNA, and gene), antisense, decoy, antibody or vaccine and so on. The dose of the other medicaments can be accordingly selected as a standard of clinical dose. Additionally, the compounding ratio of $EP_4$ agonist of the present invention and the other medicaments can be accordingly selected by the age and body weight of administering object, the administration method, the administration time, the object disease, the symptom, the combination etc. For example, the other medicaments may be used from 0.0001 to 100 parts by weight relative to 1 part by weight of the medicament of the present invention. The other medicaments may be administered in combination, for example, any one or more compounds selected from the following same or different group at appropriate ratios. The other medicaments to compensate for and/or enhance the treatment effect of the compound represented by formula (I) do not only include ones which have ever been found but ones which will be found from now based on the above-mentioned mechanism.

The other medicaments include, for example, phosphodiesterase type 4 inhibitors, steroids, β agonists, leukotriene receptor antagonists, thromboxane synthase inhibitors, thromboxane $A_2$ receptor antagonists, mediator release inhibitors, antihistamines, xanthine derivatives, anticholinergic drugs, cytokine inhibitors, prostaglandins, forskolin preparations, elastase inhibitors, metalloproteinase inhibitors, expectorants, antibiotics or immunosuppressives etc.

Examples of phosphodiesterase type 4 inhibitors include rolipram, cilomilast, Bay19-8004, NIK-616, roflumilast (BY-217), cipamfylline (BRL-61063), Atizoram (CP-80633), SCH-351591, YM-976, V-11294A, PD-168787, D-4396, IC-485 or the like.

Examples of steroid include internal or injectable steroid such as cortisone acetate, hydrocortisone, hydrocortisone sodium phosphate, hydrocortisone sodium succinate, fludrocortisone acetate, prednisolone, prednisolone acetate, prednisolone sodium succinate, prednisolone butylacetate, prednisolone sodium phosphate, halopredone acetate, methylprednisolone, methylprednisolone acetate, methylprednisolone sodium succinate, triamcinolone, triamcinolone acetate, triamcinolone acetonide, dexamethasone, dexamethasone acetate, dexamethasone sodium phosphate, dexamethasone palmitate, paramethason acetate or betamethasone, inhalation steroid such as beclometasone dipropionate, fluticasone propionate, budesonide, flunisolide, triamcinolone, ST-126P, ciclesonide, dexamethasone, mometasone furoate, prasterone sulfonate, deflazacort, methylprednisolone suleptanate, methylprednisolone sodium succinate.

Examples of β agonist include fenoterol hydrobromide, salbutamol sulfate, terbutaline sulfate, formoterol fumarate, salmeterol xinafoate, isoproterenol sulfate, orciprenaline sulfate, clorprenaline sulfate, epinephrine, trimetoquinol hydrochloride, hexoprenaline mesyl sulfate, procaterol hydrochloride, tulobuterol hydrochloride, tulobuterol, pirbuterol hydrochloride, clenbuterol hydrochloride, mabuterol hydrochloride, ritodrine hydrochloride, bambuterol, dopexamine hydrochloride, meluadrine tartrate, AR-C68397, levosalbutamol, KUR-1246, KUL-7211, AR-C89855, S-1319 or the like.

Examples of leukotriene receptor antagonist include pranlukast hydrate, montelukast, zafirlukast, seratrodast, MCC-847, KCA-757, CS-615, YM-158, L-740515, CP-195494, LM-1484, RS-635, A-93178, S-36496, BIIL-284, ONO-4057 or the like.

Examples of thromboxane $A_2$ receptor antagonist include seratrodast, ramatroban, domitroban calcium hydrate, KT-2-962 or the like.

Examples of mediator release inhibitor include tranilast, sodium cromoglicate, amlexanox, repirinast, ibudilast, dazanolast, pemirolast potassium or the like.

Examples of antihistamine include ketotifen fumarate, mequitazine, azelastine hydrochloride, oxatomide, terfenadine, emedastine difumarate, epinastine hydrochloride, astemizole, ebastine, cetirizine hydrochloride, bepotastine, fexofenadinehydrochloride, loratadine, desloratadine, olopatadine hydrochloride, TAK-427, ZCR-2060, NIP-530, mometasone furoate, mizolastine, BP-294, andolast, auranofin, acrivastine or the like.

Examples of xanthine derivative include aminophylline, theophylline, doxophylline, cipamphylline, diprophylline or the like.

Examples of anticholinergic drug include ipratropium bromide, oxitropium bromide, flutropium bromide, cimetropium bromide, temiverine, tiotropium bromide, revatropate (UK-112166) or the like.

Examples of cytokine inhibitor include suplatast tosilate or the like.

Examples of elastase inhibitor include sivelestat, ONO-6818, MR-889, PBI-1101, EPI-HNE-4, R-665 or the like.

Examples of expectorant include foeniculated ammonia spirit, sodium bicarbonate, bromhexine hydrochloride, carbocisteine, ambroxol hydrochloride, sustained preparation of ambroxol hydrochloride, methylcysteine hydrochloride, acetylycysteine, L-cysteine ethyl ester hydrorochloride, tyloxapol or the like.

Examples of antibiotic include cefuroxime sodium, meropenem trihydrate, netilmicin sulfate, sisomycin sulfate, ceftibuten, PA-1806, IB-367, tobramycin, PA-1420, doxorubicin, astromicin sulfate, cefetamet pivoxil hydrochloride and the like. Examples of antibiotic for inhalation include PA-1806, IB-367, tobramycin, PA-1420, doxorubicin, astromicin sulfate, cefetamet pivoxil hydrochloride or the like.

Examples of immunosuppressive include cyclosporine, tacrolimus, azathioprine, methotrexate, cyclophosphamide or the like.

The other medicaments to compensate for and/or enhance the preventive and/or treatment effect of the compound represented by formula (I) do not only include ones which have ever been found but ones which will be found from now based on the above-mentioned mechanism.

The pharmaceutical composition for inhalation of the present invention can be produced by adding an additive permissible for pharmaceuticals, and by forming a preparation with a technology which is commonly utilized for a single preparation or a combination preparation to the compound represented by formula (I).

The pharmaceutical composition for inhalation of the present invention preferably shows a specific activity in the tissues around trachea such as bronchus, trachea and lung for the purpose of dose reduction and by-effect reduction.

The doses to be administered are differently determined depending upon, for example, age, body weight, symptom, the desired therapeutic effect, the route of administration, and the duration of the treatment etc. In the human adult, the doses per person are generally from 1 ng to 100 mg, by inhalation administration (via lung or airway), from one time to several times per day.

As mentioned above, the doses vary depending upon various conditions. Therefore, there are cases in which doses lower than the above described doses are enough or more administration is necessary greater doses than the ranges specified above.

The preparation forms of the pharmaceutical composition for inhalation of the present invention include inhalation preparations, such as an aerosol, an inhalation powder preparation, an inhalation liquid preparation such as inhalation solution, an inhalation suspension and the like, or an encapsulated inhalation preparation. Such inhalation liquid preparations may be in a form to be dissolved or suspended in water or another suitable solvent when they are used. Such inhalation preparations can be administered with an appropriate inhalation container, such as a sprayer (atomizer or nebulizer and the like) in case of an inhalation liquid preparation, or an inhalation administrator for powder preparation in case of an inhalation powder preparation.

Such inhalation preparations can be according to publicly known methods. For example, these can be produced by forming the compound represented by formula (I) into powder or liquid and blending it in an inhalation propellant and/or a carrier, followed by filling it in an appropriate inhalation container. In case of forming the compound represented by formula (I) into powder, it can be formed into powder according to the ordinary method. For example it is formed into fine powder with lactose, starch, magnesium stearate or the like to obtain a uniform mixture, or followed by granulation to obtain a powder preparation. Also in case of forming the compound represented by formula (I) into a liquid, said compound may be dissolved in a liquid carrier such as water, physiological saline or an organic solvent. As the propellant, an already known propellant such assubstitute flon, a liquefied gas propellant such as fluorinated hydrocarbon, liquefied petroleum, diethyl ether, dimethyl ether and the like, a compressed gas such as a soluble gas such as carbon dioxide gas, nitrous oxide gas and the like or an insoluble gas such as nitrogen gas and the like, and the like can be used.

Furthermore, in the inhalation preparation, an additive may be suitably blended if necessary. The additive may be any additive which is ordinarily utilized and it may be for example a solid excipient such as white sugar, lactose, glucose, mannitol, sorbitol, maltose, cellulose and the like, a liquid filler such as propylene glycol and the like, a binder such as starch, dextrin, methylcellulose, hydroxypropylcellulose, polyvinylpyrrolidone, polyethylene glycol, white sugar and the like, a lubricant such as magnesium stearate, light silicic anhydride, talc, sodium laurylsulfate and the like, a taste-masking agent such as citric acid, menthol, ammonium glycyrrhizinate, glycin, orange powder, and the like, a preservative such as sodium benzoate, sodium hydrogensulfite, methylparaben, propylparaben and the like, a stabilizer such as citric acid, sodium citrate, and the like, a suspending agent or an emulsifier such as methylcellulose, polyvinylpyrrolidone, polyvinyl alcohol, lecithin, sorbitan trioleate and the like, a dispersant such as a surfactant and the like, a solvent such as water and the like, an isotonizing agent such as sodium chloride, concentrated glycerin and the like, a pH regulating agent such as hydrochloric acid, sulfuric acid and the like, a solubilizing agent such as ethanol and the like, an antiseptic such as benzalconium chloride, paraben and the like, a colorant, a buffer such as sodium phosphate, sodium acetate and the like, a viscosifier such as carboxyvinyl polymer and the like and an absorption promoter. For example, an inhalation liquid preparation is prepared by suitably selecting an antiseptic, a colorant, a buffer, an isotonizing agent, a viscosifier, an absorption promoter and the like according to the necessity. Also an inhalation powder preparation is prepared by suitably selecting a lubricant, a binder, a filler, a colorant, an antiseptic, an absorption promoter such as a bile salt, chitosan and the like, and the like, according to the necessity.

Also in order to provide the compound represented by formula (I) with a sustained-release property, the inhalation preparation may contain a biodegradable polymer. Examples of the biodegradable polymer include a polymer or a copolymer of a fatty acid ester, a variety of polyacrylic acid ester, a variety of polyhydroxybutyric acid, a variety of polyalkylene oxalate, polyorthoester, polycarbonate and a variety of polyamino acids, and these may be used singly or as a mixture of plural kinds. A phospholipid such as egg yolk lecithin or chitosan may be also used. Examples of the polymer or copolymer of fatty acid ester include polylactic acid, polyglycolic acid, polycitric acid, polymalic acid and a lactic acid-glycolic acid copolymer, and these may be used singly or as a mixture of plural kinds. Additionally, a poly-α-cyanoacrylic acid ester, poly-β-hydroxybutyric acid, polytrimethylene oxalate, polyorthoester, polyorthocarbonate, polyethylene carbonate, poly-γ-benzyl-L-glutamic acid or poly-L-alanine may be used singly or in a mixture of plural kinds. Polylactic acid, polyglycolic acid or a lactic acid-glycolic acid copolymer is preferred, and a lactic acid-glycolic acid copolymer is more preferred. Additionally, microspheres or nanospheres incorporating an agent may be prepared by a biodegradable polymer such as lactic acid-glycolic acid copolymer and the like.

EXAMPLES

The present invention is explained below in detail based on Examples, but the present invention is not limited thereto.

In chromatographic separations and TLC, the solvents in parenthesis show the eluting and developing solvents and the ratios of the solvents used are by volume.

Unless otherwise specified, NMR data is $^1$H-NMR data.

The solvents in parenthesis in NMR show the solvents used for measurement.

All the compounds described in the present specification were named using ACD/Name (registered trademark: Advanced Chemistry Development Inc.) or ACD/Name Batch (registered trademark: Advanced Chemistry Development Inc.) which names generally on the basis of IUPAC, or named according to IUPAC nomenclature system. For example, a compound represented by

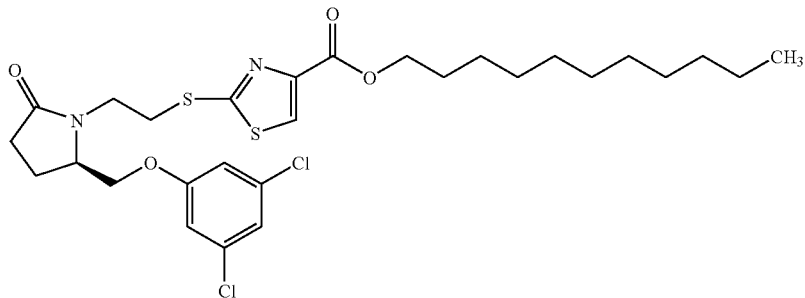

was named undecyl 2-[(2-{(2R)-2-[(3,5-dichlorophenoxy)methyl]-5-oxo-1-pyrrolidinyl}ethyl)sulfanyl]-1,3-thiazole-4-carboxylate.

A carboxylic acid derivative used as the source material in Example is described in WO03/74483. For example, 2-[(2-{(2R)-2-[(3,5-dichlorophenoxy)methyl]-5-oxopyrrolidin-1-yl}ethyl)thio]-1,3-thiazole-4-carboxylic acid is prepared in Example 6(32) of WO03/74483.

Example 1

5-[(1Z)-1-hepten-1-yl]-2-methylphenol

Under an atmosphere of Argon, to a solution of n-hexylphosphonium bromide (1.07 g) in tetrahydrofuran (10 mL) was added potassium t-butoxide (336 mg) at room temperature and the solution was stirred for 30 minutes. After cooling in ice bath, 3-hydroxy-4-methylbenzaldehyde (136 mg) was added to the reaction solution, which was stirred at room temperature for 1.5 hours. The reaction solution was diluted with t-butyl methyl ether. The solution was washed with dilute hydrochloric acid, water and brine, dried over anhydrous sodium sulfate and concentrated. The obtained residue was purified by column chromatography on silica gel (ethyl acetate:hexane=1:4) to give the title compound (180 mg) having the following physical data.

TLC: Rf 0.63 (ethyl acetate:hexane=1:4).

Example 2

5-heptyl-2-methylphenol

To a solution of the compound prepared in Example 1 (180 mg) in ethanol (5 mL) was added platinum-carbon (10 mg) and the solution was stirred at 60° C. for 7 hours under an atmosphere of hydrogen. After cooling to room temperature, the solution was filtrated through Celite (brand name) and washed with chloroform. The filtrate was concentrated to give the title compound (181 mg) having the following physical data.

TLC: Rf 0.62 (ethyl acetate:hexane=1:4).

Example 3 butyl 2-{[2-((2R)-2-{[(methylsulfonyl)oxy]methyl}-5-oxo-1-pyrrolidinyl)ethyl]thio}-1,3-thiazole-4-carboxylate To a solution of butyl 2-{[2-((2R)-2-(hydroxymethyl)-5-oxo-1-pyrrolidinyl]ethyl}thio)-1,3-thiazole-4-carboxylate (100 mg; the compound described in Reference Example 19 of WO03/74483) and triethylamine (0.070 mL) in anhydrous tetrahydrofuran (3 mL) was cooled in ice under an atmosphere of Argon. Methane sulfonylchrolide (0.026 mL) was added thereto and the solution was stirred for 30 minutes. The suspension was diluted with t-butyl methyl ether. The solution was washed dilute hydrochloric acid, water, a saturated aqueous sodium hydrogen carbonate solution and brine, dried over anhydrous sodium sulfate and concentrated to give the title compound (122 mg) having the following physical data.

TLC: Rf 0.45 (ethyl acetate:hexane=1:1).

Example 4 butyl 2-{[2-((2R))-2-[(5-heptyl-2-methylphenoxy)methyl]-5-oxo-1-pyrrolidinyl}ethyl)thio]-1,3-thiazole-4-carboxylate

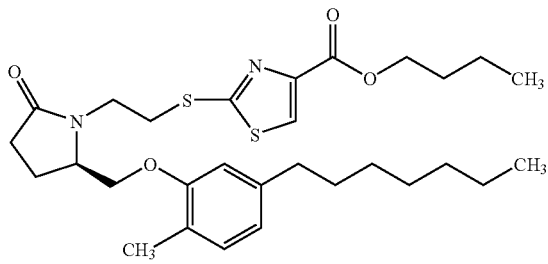

To a solution of the compound prepared in Example 2 (31 mg) and the compound prepared in Example 3 (43 mg) in anhydrous dimethylformamide (2 mL) was added cesium carbonate (65 mg) and the solution was stirred at 60° C. overnight under an atmosphere of Argon. The reaction solution was diluted with t-butyl methyl ether. The solution was washed with dilute hydrochloric acid, water and brine, dried over anhydrous sodium sulfate and concentrated. The obtained residue was purified by column chromatography on silica gel (ethyl acetate:hexane=1:4→1:1) to give the title compound (34 mg) having the following physical data.

TLC: Rf 0.81 (ethyl acetate:hexane=1:1).

Example 5

2-[(2-{(2R)-2-[(5-heptyl-2-methylphenoxy)methyl]-5-oxo-1-pyrrolidinyl}ethyl)sulfanyl]-1,3-thiazole-4-carboxylic acid

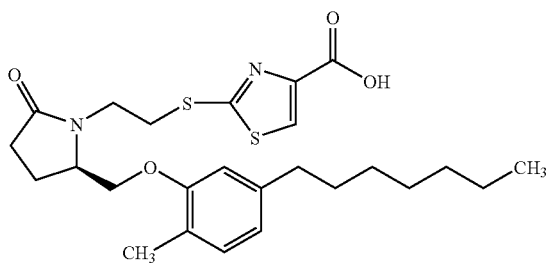

To a solution of the compound prepared in Example 4 (34 mg) in methanol (1 mL)-tetrahydrofuran (2 mL) was added 2N aqueous sodium hydroxide solution (1 mL) at room temperature and the solution was stirred for 2 hours. The reaction solution was acidified with 1N hydrochloric acid and extracted with ethyl acetate. The organic layer was washed with water and brine, dried over anhydrous sodium sulfate and concentrated to give the compound of the present invention (28 mg) having the following physical data.

TLC: Rf 0.36 (chloroform:methanol=9:1);
NMR (CDCl$_3$): δ 0.78-0.95 (m, 3H), 1.19-1.40 (m, 8H), 1.47-1.67 (m, 2H), 1.89-2.05 (m, 1H), 2.16 (s, 3H), 2.17-2.38 (m, J=20.22, 8.14 Hz, 1H), 2.37-2.72 (m, 4H), 3.15-3.33 (m, 1H), 3.42-3.61 (m, J=13.17, 5.12 Hz, 1H), 3.75-3.87 (m, 1H), 3.87-4.05 (m, 2H), 4.05-4.22 (m, 2H), 6.61 (s, 1H), 6.72 (d, J=7.50 Hz, 1H), 7.05 (d, J=7.50 Hz, 1H), 8.07 (s, 1H).

Example 5(1)-(5)

By the same procedure as a series of reactions of Example 4 Example 5 using a corresponding alcohol derivative instead of the compound prepared in Example 2, the following compounds of the present invention were obtained.

Example 5(1)

2-[(2-{(2R)-2-[(4-heptyl-2,6-dimethylphenoxy)methyl]-5-oxo-1-pyrrolidinyl}ethyl)sulfanyl]-1,3-thiazole-4-carboxylic acid TLC: Rf 0.30 (chloroform:methanol=9:1);
NMR (CDCl$_3$): δ0.81-0.95 (m, 3H), 1.17-1.39 (m, 8H), 1.43-1.65 (m, 1H), 1.83-2.07 (m, 2H), 2.13-2.31 (m, 7H), 2.31-2.68 (m, 4H), 3.37-3.56 (m, 2 H), 3.59-3.80 (m, 2H), 3.82-3.97 (m, 1H), 4.01-4.30 (m, 2H), 6.81 (s, 2H), 8.08 (s, 1H).

Example 5(2)

2-[(2-{(2R)-2-[(4-chloro-2-heptylphenoxy)methyl]-5-oxo-1-pyrrolidinyl}ethyl)sulfanyl]-1,3-thiazole-4-carboxylic acid TLC: Rf 0.30 (chloroform:methanol=9:1);
NMR (CDCl$_3$): δ 0.79-0.95 (m, 3H), 1.14-1.39 (m, 8H), 1.42-1.63 (m, 2H), 1.87-2.05 (m, 1H), 2.17-2.35 (m, 1H), 2.36-2.69 (m, 4H), 3.13-3.33 (m, 1 H), 3.38-3.56 (m, 1H), 3.62-3.82 (m, 1H), 3.83-4.03 (m, 2H), 4.03-4.22 (m, 2H), 6.66-6.81 (m, 1H), 7.03-7.17 (m, 2H), 8.07 (s, 1H).

Example 5(3)

2-[(2-{(2R)-2-[(3-chloro-4-heptylphenoxy)methyl]-5-oxo-1-pyrrolidinyl}ethyl)sulfanyl]-1,3-thiazole-4-carboxylic acid TLC: Rf 0.28 (chloroform:methanol=9:1);
NMR (CDCl$_3$): δ 0.82-0.96 (m, 3H), 1.18-1.41 (m, 8H), 1.45-1.67 (m, 2H), 1.84-2.02 (m, 1H), 2.14-2.32 (m, 1H), 2.34-2.50 (m, 1H), 2.50-2.73 (m, 3 H), 3.15-3.35 (m, 1H), 3.42-3.58 (m, 1H), 3.76 (dd, J=10.34, 5.03 Hz, 1H), 3.82-4.01 (m, 2H), 4.00-4.19 (m, 2H), 6.71 (dd, J=8.51, 2.65 Hz, 1H), 6.88 (d, J=2.74 Hz, 1H), 7.11 (d, J=8.42 Hz, 1H), 8.08 (s, 1H).

Example 5(4)

2-[(2-{(2R)-2-[(2-chloro-4-heptylphenoxy)methyl]-5-oxo-1-pyrrolidinyl}ethyl)sulfanyl]-1,3-thiazole-4-carboxylic acid TLC: Rf 0.25 (chloroform:methanol=9:1);
NMR (CDCl$_3$): δ 0.80-0.94 (m, 3H), 1.18-1.39 (m, 8H), 1.44-1.66 (m, 2H), 1.78-1.97 (m, 1H), 2.17-2.35 (m, 1H), 2.39-2.57 (m, 3H), 2.56-2.73 (m, 1 H), 3.20-3.38 (m, 1H), 3.48-3.65 (m, 1H), 3.76-3.92 (m, 1H), 3.92-4.08 (m, 2H), 4.08-4.24 (m, 2H), 6.80 (d, J=8.42 Hz, 1H), 6.95-7.07 (m, 1H), 7.17-7.24 (m, 1H), 8.03-8.10 (m, 1H).

Example 5(5)

2-[(2-{(2R)-2-[(4-heptyl-3,5-dimethylphenoxy)methyl]-5-oxo-1-pyrrolidinyl}ethyl)sulfanyl]-1,3-thiazole-4-carboxylic acid TLC: Rf 0.48 (chloroform:methanol=9:1);
NMR (CDCl$_3$): δ 0.82-0.96 (m, 3H), 1.18-1.50 (m, 10H), 1.83-2.01 (m, 1H), 2.11-2.24 (m, 1H), 2.28 (s, 6H), 2.31-2.66 (m, 4H), 3.17-3.34 (m, 1H), 3.42-3.57 (m, 1H), 3.67-3.83 (m, 1H), 3.82-3.98 (m, 2H), 3.98-4.17 (m, 2H), 6.52 (s, 2H), 8.06 (s, 1H).

Example 6 undecyl 2-[(2-{(2R)-2-[(3,5-dichlorophenoxy)methyl]-5-oxo-1-pyrrolidinyl}ethyl)sulfanyl]-1,3-thiazole-4-carboxylate

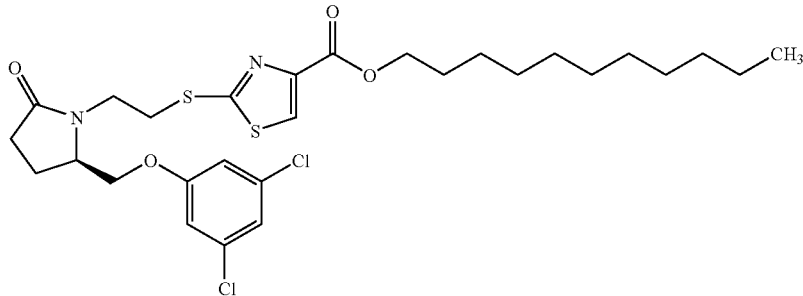

To a solution of 2-[(2-{(2R)-2-[(3,5-dichlorophenoxy)methyl]-5-oxopyrrolidin-1-yl}ethyl)thio]-1,3-thiazole-4-carboxylic acid (102 mg; the compound prepared in Example 6(32) of WO03/74483) and 1-bromoundecane (106 mg) in anhydrous dimethylformamide (5 mL) was added cesium carbonate (147 mg, 0.45 mmol) and the solution was stirred at 60° C. for 3 hours under an atmosphere of Argon. The reaction solution was diluted with t-butyl methyl ether. The solution was washed with dilute hydrochloric acid, water and brine, dried over anhydrous sodium sulfate and concentrated. The obtained residue was purified by column chromatography on silica gel (ethyl acetate:hexane=1:4→1:1) to give the compound of the present invention (131 mg) having the following physical data.

TLC: Rf 0.46 (ethyl acetate:hexane=1:1);
NMR (CDCl$_3$): δ 0.83-0.93 (m, 3H), 1.16-1.47 (m, 16H), 1.68-1.82 (m, 2H), 1.98-2.13 (m, 1H), 2.15-2.31 (m, 1H), 2.32-2.47 (m, 1H), 2.49-2.65 (m, 1 H), 3.20-3.34 (m, 1H), 3.40-3.54 (m, 1H), 3.54-3.68 (m, 1H), 3.76-3.92 (m, 1H), 4.00 (dd, J=10.43, 3.29 Hz, 1H), 4.07-4.18 (m, 1H), 4.25-4.40 (m, 2H), 4.68 (dd, J=10.34, 3.02 Hz, 1H), 6.84-6.89 (m, 2H), 6.91-6.95 (m, 1H), 7.97 (s, 1H).

Example 6(1)-(3)

By the same procedure as a series of reactions of Example 6 using a corresponding carboxylic acid derivative instead of 2-[(2-{(2R)-2-[(3,5-dichlorophenoxy)methyl]-5-oxopyrrolidin-1-yl}ethyl)thio]-1,3-thiazole-4-carboxylic acid, and a corresponding bromide or iodide instead of 1-bromoundecane, the following compounds of the present invention were obtained.

Example 6(1)

10-phenyldecyl 2-[(2-{(2R)-2-[(3,5-dichlorophenoxy)methyl]-5-oxo-1-pyrrolidinyl}ethyl)sulfanyl]-1,3-thiazole-4-carboxylate TLC: Rf 0.41 (ethyl acetate:hexane=1:1);
NMR (CDCl$_3$): δ 1.21-1.46 (m, 12H), 1.53-1.68 (m, 2H), 1.68-1.81 (m, 2H), 1.97-2.13 (m, 1H), 2.13-2.30 (m, 1H), 2.30-2.46 (m, 1H), 2.50-2.66 (m, 3 H), 3.19-3.35 (m, 1H), 3.40-3.53 (m, 1H), 3.54-3.68 (m, 1H), 3.77-3.91 (m, 1H), 4.00 (dd, J=10.34, 3.20 Hz, 1H), 4.06-4.18 (m, 1H), 4.26-4.40 (m, 2H), 4.68 (dd, J=10.25, 2.93 Hz, 1H), 6.87 (d, J=1.65 Hz, 2H), 6.92 (t, J=1.83 Hz, 1 H), 7.13-7.21 (m, 3H), 7.23-7.31 (m, 2H), 7.97 (s, 1H).

Example 6(2)

10-phenyldecyl 2-{[2-((5R)-2-oxo-5-{[3-(trifluoromethoxy)phenoxy]methyl}-1-pyrrolidinyl)ethyl]sulfanyl}-1,3-thiazole-4-carboxylate TLC: Rf 0.47 (ethyl acetate:hexane=1:1);
NMR (CDCl$_3$): δ 1.20-1.46 (m, 12H), 1.50-1.66 (m, 2H), 1.66-1.84 (m, 2H), 1.97-2.15 (m, 1H), 2.15-2.31 (m, 1H), 2.30-2.47 (m, 1H), 2.48-2.68 (m, 3 H), 3.23-3.40 (m, 1H), 3.41-3.68 (m, 2H), 3.80-3.95 (m, 1H), 4.02 (dd, J=10.25, 3.48 Hz, 1H), 4.08-4.21 (m, 1H), 4.30 (t, J=6.77 Hz, 2H), 4.56 (dd, J=10.43, 3.11 Hz, 1H), 6.73-6.90 (m, 3H), 7.10-7.34 (m, 6H), 7.96 (s, 1H).

Example 6(3)

10-phenyldecyl 2-[(2-{(2R)-2-[(1E,4S)-4-(1-ethylcyclobutyl)-4-hydroxy-1-buten-1-yl]-5-oxo-1-pyrrolidinyl}ethyl)sulfanyl]-1,3-thiazole-4-carboxylate TLC: Rf 0.32 (hexane:ethyl acetate=1:2);
NMR (CDCl$_3$): δ 0.90 (t, J=7.50 Hz, 3H), 1.24-1.47 (m, 11H), 1.54-2.04 (m, 17H), 2.13-2.48 (m, 4H), 2.56-2.63 (m, 2H), 3.35-3.56 (m, 4H), 3.72-3.89 (m, 1H), 4.14-4.24 (m, 1H), 4.31 (t, J=6.90 Hz, 1H), 5.39 (dd, J=15.40, 8.90 Hz, 1H), 5.82 (dt, J=15.40, 7.00 Hz, 1H), 7.13-7.21 (m, 3H), 7.23-7.31 (m, 2 H), 7.99 (s, 1H).

Example 7

2-({2-[(2R)-2-({[tert-butyl(dimethyl)silyl]oxy}methyl)-5-oxo-1-pyrrolidinyl]ethyl}thio)-1,3-thiazole-4-carboxylic acid To a solution of 2-(2-((2R)-2-(t-butyldimethylsilyloxymethyl)-5-oxopyrrolidin-1-yl)ethylthio)-1,3-thiazole-4-carboxylic acid ethyl ester (240 mg; the compound described in Reference Example 17 of WO03/74483) in tetrahydrofuran (4 mL)-methanol (2 mL) was added 2N aqueous sodium hydroxide solution (2 mL) at room temperature and the solution was stirred for 1 hour. The reaction solution was acidified with dilute hydrochloric acid and extracted with ethyl acetate. The organic layer was washed with brine, dried over anhydrous sodium sulfate and concentrated to give the title compound (240 mg) having the following physical data.

TLC: Rf 0.10 (chloroform:methanol=9:1).

Example 8

10-phenyldecyl 2-({2-[(2R)-2-({[tert-butyl(dimethyl)silyl]oxy}methyl)-5-oxo-1-pyrrolidinyl]ethyl}thio)-1,3-thiazole-4-carboxylate To a solution of the compound prepared in Example 7 (240 mg) and 10-iododecylbenzene (261 mg) in anhydrous dimethylformamide (5 mL) was added cesium carbonate (315 mg) and the solution stirred at 50° C. overnight under an atmosphere of Argon. The reaction solution was diluted with tert-butoxymethyl. The solution was washed with dilute hydrochloric acid, water and brine, dried over anhydrous sodium sulfate and concentrated to give the title compound (430 mg) having the following physical data.

TLC: Rf 0.87 (ethyl acetate).

Example 9

10-phenyldecyl 2-({2-[(2R)-2-(hydroxymethyl)-5-oxo-1-pyrrolidinyl]ethyl}thio)-1,3-thiazole-4-carboxylate To a solution of the compound prepared in Example 8 (430 mg) in tetrahydrofuran (3 mL) was added a solution of tetrabutylammonium fluoride in tetrahydrofuran (1.0 M, 1.1 mL) at room temperature and the solution was stirred for 1 hour. The reaction solution was diluted with ethyl acetate. The solution was washed with a saturated ammonium chloride solution and brine, dried over anhydrous sodium sulfate and concentrated. The obtained residue was purified by column chromatography on silica gel (ethyl acetate:hexane=1:1→1:0) to give the title compound (195 mg) having the following physical data.

TLC: Rf 0.28 (ethyl acetate).

Example 10

10-phenyldecyl 2-({2-[(2R)-2-formyl-5-oxo-1-pyrrolidinyl]ethyl}thio)-1,3-thiazole-4-carboxylate Under an atmosphere of Argon, a solution of the compound prepared in Example 9 (195 mg) and diisopropylethylamine (0.39 mL) in ethyl acetate (2 mL)-diimethylsulfoxide (1 mL) was cooled to 0° C. Sulfur trioxide-pyridine complex (180 mg) was added to the solution, which was stirred for 1 hour. The reaction solution was diluted with ethyl acetate. The solution was washed with dilute hydrochloric acid, water and brine, dried over anhydrous sodium sulfate and concentrated to give the title compound (200 mg) having the following physical data.

TLC: Rf 0.50 (ethyl acetate:methanol=19:1).

Example 11

10-phenyldecyl 2-[(2-{(2R)-2-[(heptylamino)methyl]-5-oxo-1-pyrrolidinyl}ethyl)sulfanyl]-1,3-thiazole-4-carboxylate hydrochloride

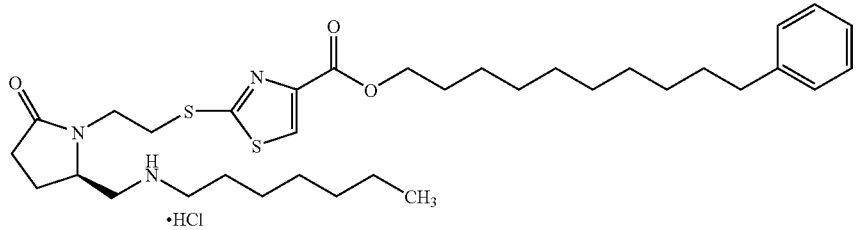

Under an atmosphere of Argon, to a solution of the compound prepared in Example 10 (200 mg) in dichloromethane (4 mL) was added heptylamine (0.11 mL) at room temperature and the solution was stirred for 1 hour. Sodium triacetoxyborohydride (159 mg) was added to the reaction solution, which was stirred for 2 hours. After the reaction was stopped by adding a saturated aqueous sodium hydrogen carbonate solution, the reaction mixture was poured into water and extracted with ethyl acetate. The reaction mixture was washed with brine, dried over anhydrous sodium sulfate and concentrated. The obtained residue was purified by column chromatography on silica gel (chloroform:methanol=100:1→30:1). The obtained oil was dissolved in ethyl acetate. 4N hydrogen chloride-ethyl acetate solution (0.1 mL) was added thereto. The mixture was concentrated to give the compound of the present invention (195 mg) having the following physical data.

TLC: Rf 0.55 (chloroform:methanol=9:1);

NMR (CD$_3$OD): δ 0.85-0.97 (m, 3H), 1.23-1.50 (m, 20H), 1.59 (s, 2H), 1.67-1.84 (m, 4H), 1.98 (d, J=16.28 Hz, 1H), 2.23-2.51 (m, 3H), 2.53-2.63 (m, 2 H), 3.03-3.23 (m, J=7.68 Hz, 4H), 3.44-3.58 (m, J=9.70 Hz, 2H), 3.60-3.71 (m, 1H), 3.76-3.91 (m, J=7.87 Hz, 1H), 4.10-4.22 (m, 1H), 4.32 (t, J=6.68 Hz, 2H), 7.01-7.42 (m, 5H), 8.29 (s, 1H).

Example 11(1)

undecyl 2-[(2-{(2R)-2-[(heptylamino)methyl]-5-oxo-1-pyrrolidinyl}ethyl)sulfanyl]-1,3-thiazole-4-carboxylate hydrochloride By the same procedure as a series of reactions of Example 8→Example 9→Example 10→Example 11 using 1-bromoundecane instead of 10-iododecylbenzene, the compound of the present invention having the following physical data was obtained.

TLC: Rf 0.19 (chloroform:methanol=9:1);
NMR (CD$_3$OD): δ 0.82-0.99 (m, 6H), 1.22-1.50 (m, 24H), 1.68-1.85 (m, 4 H), 1.87-2.05 (m, 1H), 2.22-2.54 (m, 3H), 3.02-3.28 (m, 4H), 3.43-3.61 (m, 2H), 3.67 (dd, J=12.81, 2.93 Hz, 1H), 3.76-3.95 (m, 1H), 4.17 (s, 1H), 4.28-4.39 (m, 2H), 8.16-8.42 (m, 1H).

Example 12(1)-(3)

By the same procedure as a series of reactions of Example 6 using 2-[(2-{(2R)-2-[(3,5-dichlorophenoxy)methyl]-5-oxopyrrolidin-1-yl}ethyl)thio]-1,3-thiazole-4-carboxylic acid or 2-[(2-{(2R)-2-[(1E)-1-nonenyl]-5-oxo-1-pyrrolidinyl}ethyl)sulfanyl]-1,3-thiazole-4-carboxylic acid, and a corresponding bromide or iodide instead of 1-bromoundecane, the following compounds of the present invention were obtained.

Example 12(1)

10-phenyldecyl 2-[(2-{(2R)-2-[(1E)-1-nonenyl]-5-oxo-1-pyrrolidinyl}ethyl)sulfanyl]-1,3-thiazole-4-carboxylate TLC: Rf 0.49 (hexane:ethyl acetate=1:1);
NMR (CDCl$_3$): δ 0.88 (t, J=6.60 Hz, 3H) 1.16-1.46 (m, 21H) 1.54-1.82 (m, 6 H) 1.93-2.03 (m, 2H) 2.12-2.46 (m, 3H) 2.60 (t, J=7.50 Hz, 2H) 3.24-3.36 (m, 1H) 3.37-3.52 (m, 2H) 3.78-3.88 (m, 1H) 4.09-4.19 (m, 1H) 4.32 (t, J=6.90 Hz, 2H) 5.16-5.27 (ddt, J=15.20, 9.00, 1.50 Hz, 1H) 5.66 (dt, J=15.20, 6.80 Hz, 1H) 7.13-7.21 (m, 3H) 7.23-7.31 (m, 2H) 8.00 (s, 1H).

Example 12(2)

2-(decanoyloxy)ethyl 2-[(2-{(2R)-2-[(3,5-dichlorophenoxy)methyl]-5-oxo-1-pyrrolidinyl}ethyl)sulfanyl]-1,3-thiazole-4-carboxylate TLC: Rf 0.20 (ethyl acetate:hexane=1:1);
NMR (CDCl$_3$): δ 0.82-0.92 (m, 3H) 1.17-1.37 (m, 12H) 1.54-1.68 (m, 2H) 1.99-2.14 (m, 1H) 2.15-2.28 (m, 1H) 2.32 (t, J=7.50 Hz, 2H) 2.36-2.47 (m, 1 H) 2.50-2.66 (m, 1H) 3.19-3.32 (m, 1H) 3.40-3.54 (m, 1H) 3.54-3.68 (m, 1H) 3.77-3.90 (m, 1H) 4.00 (dd, J=10.34, 3.20 Hz, 1H) 4.06-4.16 (m, 1H) 4.33-4.48 (m, 2H) 4.52 (q, J=4.45 Hz, 2H) 4.68 (dd, J=10.25, 2.93 Hz, 1H) 6.87 (d, J=1.83 Hz, 2H) 6.92 (t, J=1.83 Hz, 1H) 7.99 (s, 1H).

Example 12(3)

10-hydroxydecyl 2-[(2-{(2R)-2-[(3,5-dichlorophenoxy)methyl]-5-oxo-1-pyrrolidinyl}ethyl)sulfanyl]-1,3-thiazole-4-carboxylate TLC: Rf 0.32 (ethyl acetate);
NMR (CDCl$_3$): δ 1.22-1.46 (m, 16H) 1.69-1.83 (m, 2H) 1.94-2.15 (m, 1H) 2.15-2.47 (m, 2H) 2.48-2.68 (m, 1H) 3.19-3.35 (m, 1H) 3.35-3.55 (m, 1H) 3.64 (t, J=6.59 Hz, 2H) 3.77-3.94 (m, 1H) 4.01 (dd, J=10.43, 3.11 Hz, 1H) 4.08-4.20 (m, 1H) 4.27-4.40 (m, 2H) 4.68 (dd, J=10.25, 3.11 Hz, 1H) 6.87 (d, J=1.83 Hz, 2H) 6.93 (t, J=1.74 Hz, 1H) 7.98 (s, 1H).

Biological Example

(1) Inhibitory Activity on Histamine-Induced Airway Contractile Response and Hypotensive Activity of Intravenous Administration or Inhalation Administration in Guinea Pig A guinea pig anesthetized with sodium pentobarbital (75 mg/kg, i.p.) was treated with gallamine (10 mg/kg, i.v.), and an experiment was carried out under artificial respiration. As an airway contraction inducing substance, histamine (10 μg/kg, i.v.) was used, and the airway contractile response was determined by the Konzett & Roessler method (Konzett, H., Roessler, R. Versuchsanordnung zu untersuchungen ander Bronchial-muskulatur. *Arch Exp Pathol Pharmacol* 1940; 195:71-74). Additionally, the blood pressure was also measured at the same time. A test substance was administered intravenously or by inhalation (the test substance or a physiological saline solution was atomized using an ultrasonic nebulizer and inhaled directly into the trachea for 5 minutes using an artificial respirator). An inhibition ratio of airway contraction (%) was calculated by taking the airway contraction induced by histamine before administration of the test substance or in a group administered with a physiological saline solution as 0% inhibition. The amount of blood pressure reduction (mmHg) was expressed as the amount of diastolic blood pressure reduction. The results are shown in FIG. 1. In the case of 2-[(2-{(2R)-2-[(1E,4S)-4-(1-ethylcyclobutyl)-4-hydroxybut-1-enyl]-5-oxopyrrolidin-1-yl}ethyl)sulfanyl]-1,3-thiazole-4-carboxylic acid (a compound described in Example 2 in WO 03/74483, hereinafter abbreviated as Compound A); 2-[(2-{(2R)-2-[(3,5-dichlorophenoxy)methyl]-5-oxopyrrolidin-1-yl}ethyl)thio]-1,3-thiazole-4-carboxylic acid (a compound described in Example 6(32) in WO 03/74483, hereinafter abbreviated as Compound B); 2-{[2-((2R)-2-{[2-chloro-3-(trifluoromethyl)phenoxy]methyl}-5-oxopyrrolidin-1-yl)ethyl]sulfanyl}-1,3-thiazole-4-carboxylic acid (a compound described in Example 6(66) in WO 03/74483, hereinafter abbreviated as Compound C); and 2-{[2-((5R)-2-oxo-5-{[3-(trifluoromethoxy)phenoxy]methyl}pyrrolidin-1-yl)ethyl]sulfanyl}-1,3-thiazole-4-carboxylic acid (a compound described in Example 6(74) in WO 03/74483, hereinafter abbreviated as Compound D), which are the pharmaceutical compositions for inhalation of the present invention, a dissociation between the inhibitory effect on airway contraction and the hypotensive effect became larger by inhalation administration than by intravenous administration. From this, it was shown that the pharmaceutical composition for inhalation of the present invention has an inhibitory effect on airway contraction and its hypotensive effect is small.

(2) Effect of Compound of the Present Invention by Intratracheal Administration on Methacholine-Induced Airway Contractile Response in Guinea Pig A test substance was intratracheally administered to a guinea pig anesthetized with GOI (laughing gas:oxygen=3:1, 3% isoflurane) using a tube for intratracheal administration. After a certain period of time, the guinea pig was anesthetized with sodium pentobarbital (50 mg/kg, i.p.) and treated with gallamine (10 mg/kg, i.v.). Then, the resulting airway contractile response was determined under artificial respiration. As an airway contraction inducing substance, methacholine (10 μg/kg, i.v.) was used, and the airway contractile response was determined by the Konzett & Roessler method. A ratio of airway contraction (% of maximum) was calculated by taking the airway response obtained by closing a three-way stopcock attached to an upper part of a cannula inserted into the tracheal tube of the guinea pig as 100%. The results are shown in FIGS. 2 to 5. Although Compound B which is an EP2 agonist having a carboxyl group has a bronchodilator effect, the effect was lost at around 3 hours after the administration. On the other hand, butyl 2-[(2-{(2R)-2-[(3,5-dichlorophenoxy)methyl]-5-oxopyrrolidin-1-yl}ethyl)thio]-1,3-thiazole-4-carboxylate (a compound described in Example 5(32) in WO 03/74483, hereinafter abbreviated as Compound E), which is a butyl ester of Compound B, showed a more prolonged duration of activity compared with Compound B. Additionally, undecyl 2-[(2-{(2R)-2-[(3,5-dichlorophenoxy)methyl]-5-oxopyrrolidin-1-yl}ethyl)sulfanyl]-1,3-thiazole-4-carboxylate (a compound described in Example 6, hereinafter abbreviated as Compound F), or 10-phenyldecyl 2-[(2-{(2R)-2-[(3,5-dichlorophenoxy)methyl]-5-oxopyrrolidin-1-yl}ethyl)sulfanyl]-1,3-thiazole-4-carboxylate (a compound described in Example 6(1), hereinafter abbreviated as Compound G), which are a longer chain ester, showed a more prolonged duration of activity compared with Compound F. From this, it was shown that the pharmaceutical composition for inhalation with high lipid solubility has a more prolonged duration of activity.

(3) Bronchodilator Effect and Hypotensive Effect of a Sustained Prodrug of EP2 Agonist A guinea pig anesthetized with sodium pentobarbital (50 mg/kg, i.p.) was treated with gallamine (10 mg/kg, i.v.), and an experiment was carried out under artificial respiration. As an airway contraction inducing substance, methacholine (10 μg/kg, i.v.) was used, and the airway contractile response was determined by the Konzett & Roessler method. Compound B was dissolved in an equimolar amount of sodium hydroxide and diluted with a physiological saline solution. Compound F was suspended in a physiological saline solution containing 2% ethanol and 10% Tween 80 to prepare a test substance. The test substance was intratracheally administered using a tube for intratracheal administration. After the administration of the test substance, the blood pressure and the airway contractile response were measured for 12.5 minutes and 3 hours, respectively. A ratio of airway contraction (%) was calculated by taking the airway response obtained by closing a three-way stopcock attached to an upper part of a cannula inserted into the tracheal tube of the guinea pig as 100% contraction. The amount of blood pressure reduction (mmHg) was expressed based on the blood pressure before administration of the test substance. The results are shown in FIGS. 6 to 9. Compound F, which is an undecyl ester of Compound B, did not change the blood pressure and showed a prolonged duration of bronchodilator activity compared with Compound B. From this, it was shown that the sustained prodrug has a long duration of a bronchodilator effect, which is a main effect, and can reduce a hypotensive effect.

Formulation Example

The typical formulation example used in the present invention was described below.

Formulation Example 1

The following constituent was mixed to give a solution for inhalation.
compound F (undecyl 2-[(2-{(2R)-2-[(3,5-dichlorophenoxy)methyl]-5-oxopyrrolidin-1-yl}ethyl)sulfanyl]-1,3-thiazole-4-carboxylate)(40 mg)
purified water (1000 mL)

Formulation Example 2

After the compound F (5.6 g) and maltose (400 g) was dissolved into purified water, to the mixture was added disodium hydrogen phosphate 12-hydrate (20 g) and thereto was added distilled water to fill up to 4000 mL. The solution was freeze-dried by a conventional method and crushed to give a powder for inhalation.

INDUSTRIAL APPLICABILITY

A medicinal composition for inhalation containing a sustained prodrug of an EP2 agonist topically exhibits a prolonged bronchodilating and antiinflammatory effects. Namely, the pharmaceutical composition for inhalation containing a sustained prodrug of an EP2 agonist is useful as a safe preventive and/or treatment agent for respiratory diseases (for example, asthma, pulmonary injury such as acute pulmonary injury and chronic injury, pulmonary fibrosis, pulmonary emphysema, bronchitis such as acute bronchitis and chronic bronchitis, chronic obstructive pulmonary disease, adult respiratory distress syndrome, cystic fibrosis, pulmonary hypertension or the like) without causing any systemic effect such as blood pressure reduction.

Figure 1:
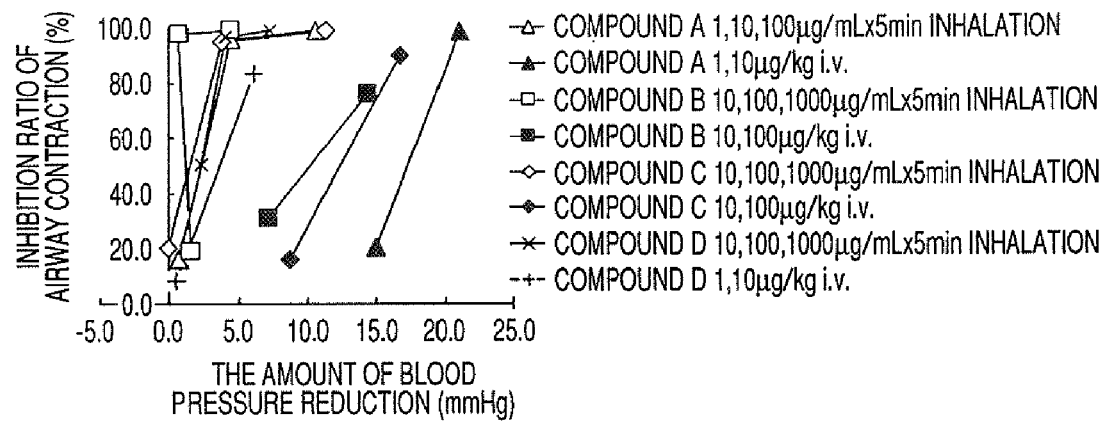
[FIG. 1] Inhibitory effect on airway contraction and hypotensive effect of the pharmaceutical composition of the present invention in intravenous administration or inhalation are indicated.
Figure 2:
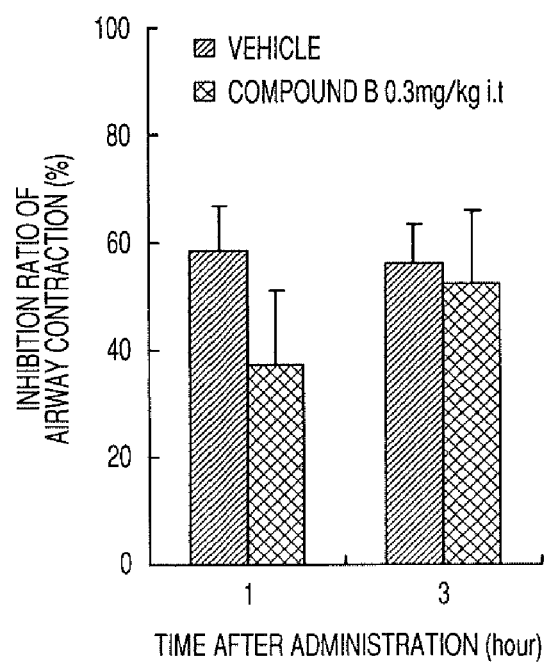
[FIG. 2] Inhibitory effect on airway contraction and the duration of effect of the compound B are indicated.
Figure 3:
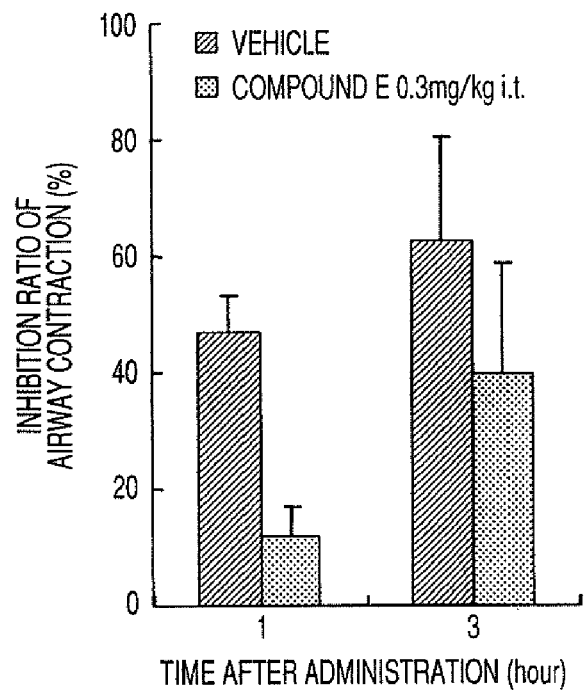
[FIG. 3] Inhibitory effect on airway contraction and the duration of effect of the compound E are indicated.
Figure 4:
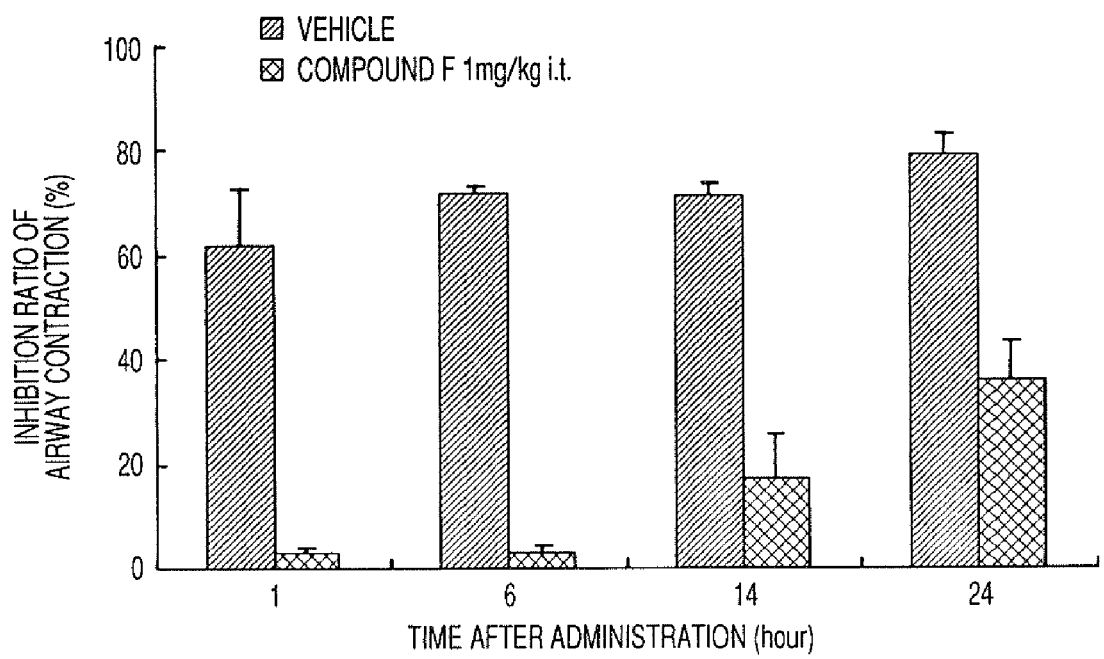
[FIG. 4] Inhibitory effect on airway contraction and the duration of effect of the compound F are indicated.
Figure 5:
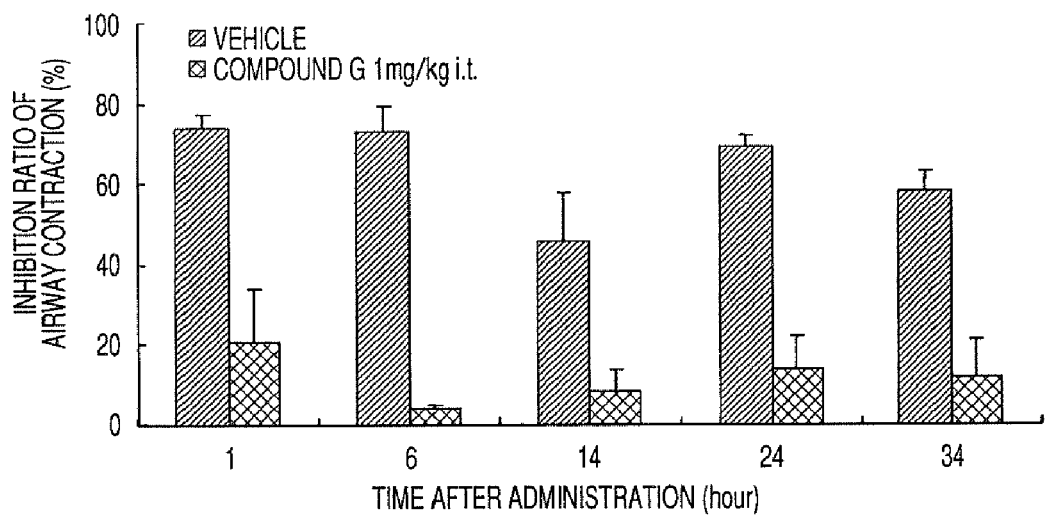
[FIG. 5] Inhibitory effect on airway contraction and the duration of effect of the compound G are indicated.
Figure 6:
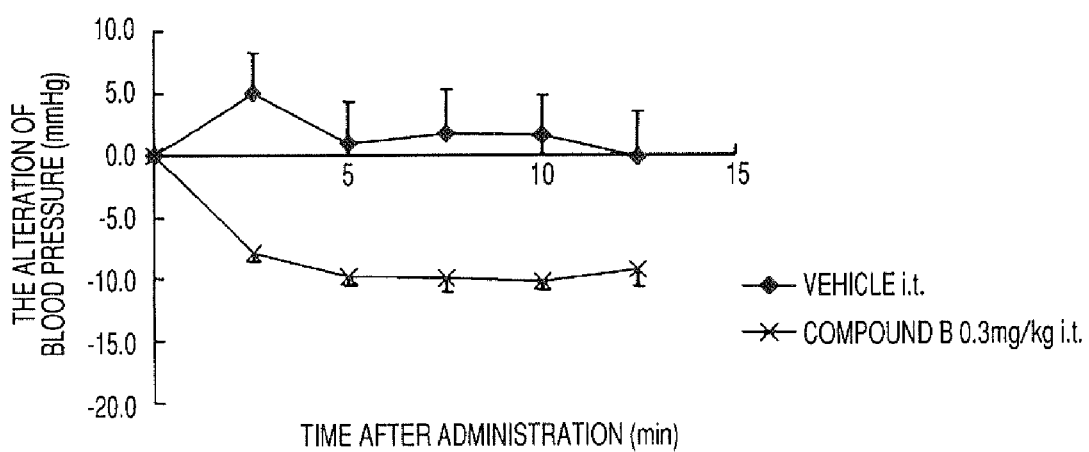
[FIG. 6] The alteration of blood by the compound B is indicated.
Figure 7:
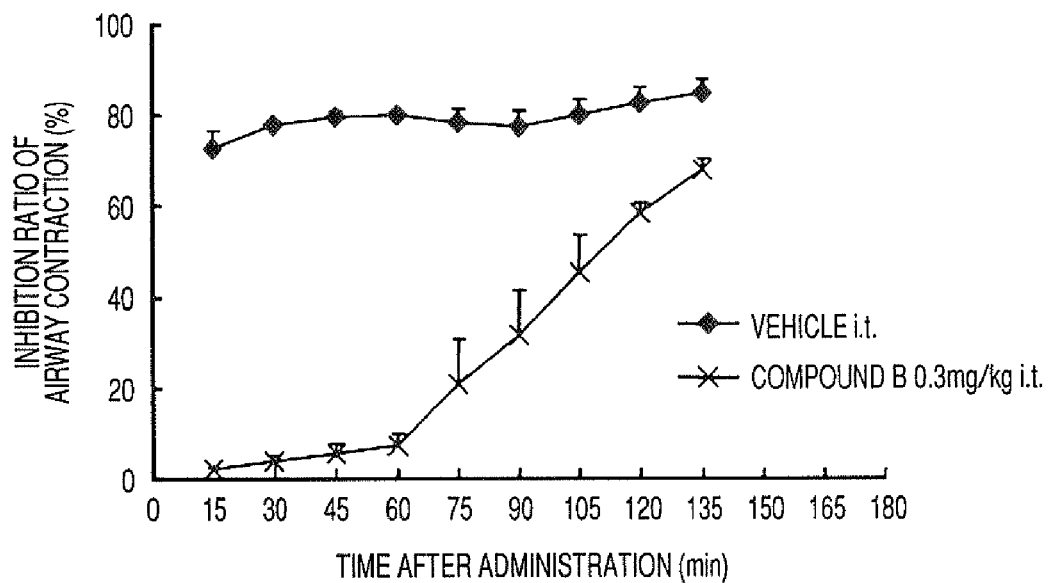
[FIG. 7] Inhibitory effect on airway contraction and the duration of effect of the compound B are indicated.
Figure 8:
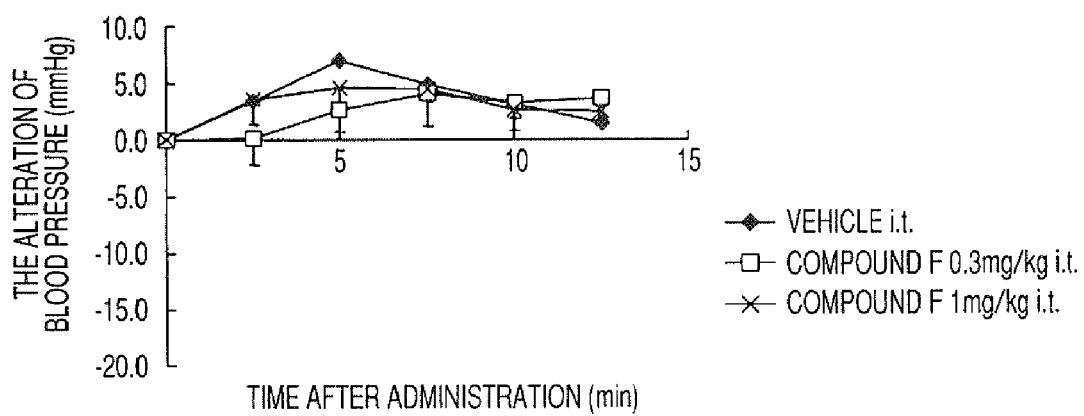
[FIG. 8] The alteration of blood pressure by the compound F is indicated.
Figure 9:
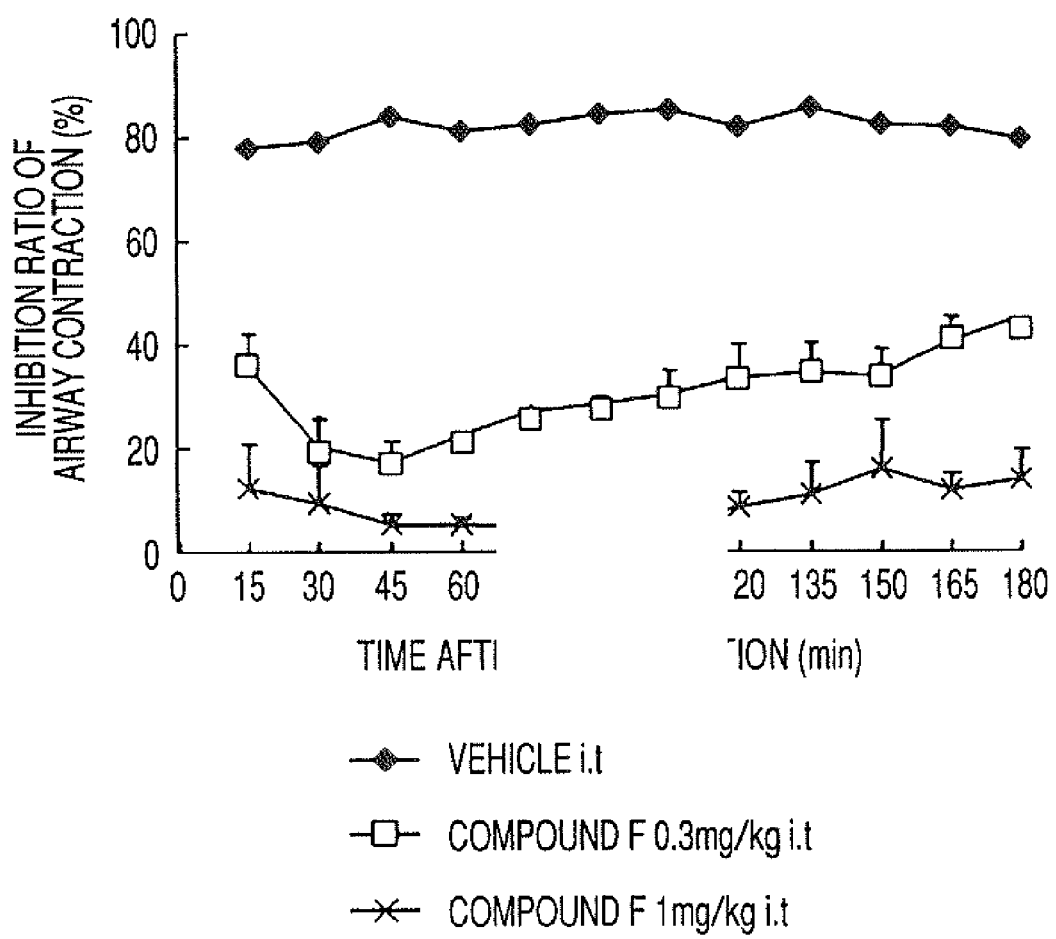
[FIG. 9] Inhibitory effect on airway contraction and the duration of effect of the compound F are indicated.

The invention claimed is:
1. A pharmaceutical composition for inhalation comprising a compound represented by formula (I-1a):

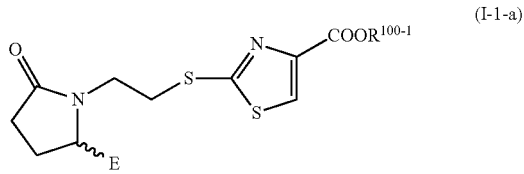

(I-1-a)

wherein $R^{100\text{-}1}$ is C11-20 alkyl which may have a substituent(s), C7-20 alkenyl which may have a substituent(s) or C7-20 alkynyl which may have a substituent(s);

E is $E^1$ or $E^2$, $E^1$ is

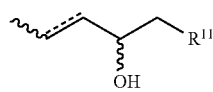

$R^{11}$ is (1) C1-10 alkyl, (2) C1-10 alkylthio, (3) C1-10 alkyl substituted by C3-8 cycloalkyl, (4) C1-10 alkyl substituted by ring 2 or (5) C1-10 alkyl substituted by —$W^1$—$W^2$-ring 2, $W^1$ is (1) —O—, (2) —S—, (3) —SO—, (4) —$SO_2$—, (5) —$NR^{11\text{-}1}$—, (6) carbonyl, (7) —$NR^{11\text{-}1}SO_2$—, (8) carbonylamino or (9) aminocarbonyl, $R^{11\text{-}1}$ is (1) a hydrogen atom, (2) C1-10 alkyl or (3) C2-10 acyl, $W^2$ is (1) a bond or (2) C1-8 alkyl optionally substituted by C1-4 alkyl, a halogen atom or hydroxy, $E^2$ is (1) —$U^1$—$U^2$—$U^3$ or (2) ring 4, $U^1$ is (1) C1-4 alkylene, (2) C2-4 alkenylene, (3) C2-4 alkynylene, (4) -ring 3-, (5) C1-4 alkylene-ring 3-, (6) C2-4 alkenylene-ring 3- or (7) C2-4 alkynylene-ring 3-, $U^2$ is (1) a bond, (2) —$CH_2$—, (3) —CHOH—, (4) —O—, (5) —S—, (6) —SO—, (7) —$SO_2$—, (8) —$NR^{12}$—, (9) carbonyl, (10) —$NR^{12}SO_2$—, (11) carbonylamino or (12) aminocarbonyl, $R^{12}$ is (1) a hydrogen atom, (2) C1-10 alkyl or (3) C2-10 acyl, $U^3$ is (1) C1-8 alkyl optionally substituted by 1 to 3 substituent(s) selected from C1-10 alkyl, halogen atom, hydroxy, C1-10 alkoxy, C1-10 alkylthio and $NR^{13}R^{14}$, (2) C2-8 alkenyl optionally substituted by 1 to 3 substituent(s) selected from C1-10 alkyl, a halogen atom, hydroxy, C1-10 alkoxy, C1-10 alkylthio and $NR^{13}R^{14}$, (3) C2-8 alkynyl optionally substituted by 1 to 3 substituent(s) selected from C1-10 alkyl, a halogen atom, hydroxy, C1-10 alkoxy, C1-10 alkylthio and $NR^{13}R^{14}$, (4) C1-8 alkyl substituted by ring 4 or (5) ring 4, $R^{13}$ and $R^{14}$ are each independently (1) a hydrogen atom or (2) C1-10 alkyl, ring 2, ring 3 and ring 4 are each independently optionally substituted by 1 to 5 R, R is (1) C1-10 alkyl, (2) C2-10 alkenyl, (3) C2-10 alkynyl, (4) C1-10 alkoxy, (5) C1-10 alkylthio, (6) halogen atom, (7) hydroxy, (8) nitro, (9) —$NR^{15}R^{16}$, (10) C1-10 alkyl substituted by C1-10 alkoxy, (11) C1-10 alkyl substituted by 1 to 3 halogen atom(s), (12) C1-10 alkyl substituted by C1-10 alkoxy substituted by 1 to 3 halogen atom(s), (13) C1-10 alkyl substituted by —$NR^{15}R^{16}$, (14) ring 5, (15) —O-ring 5, (16) C1-10 alkyl substituted by ring 5, (17) C2-10 alkenyl substituted by ring 5, (18) C2-10 alkynyl substituted by ring 5, (19) C1-10 alkoxy substituted by ring 5, (20) C1-10 alkyl substituted by —O-ring 5, (21) —$COOR^{17}$, (22) C1-10 alkoxy substituted by 1 to 4 halogen atom(s), (23) formyl, (24) C1-10 alkyl substituted by hydroxy or (25) C2-10 acyl, $R^{15}$, $R^{16}$ and $R^{17}$ are each independently (1) hydrogen atom or (2) C1-10 alkyl, ring 5 may be substituted by 1 to 3 substituent(s) selected from the following (1) to (9); (1) C1-10 alkyl, (2) C2-10 alkenyl, (3) C2-10 alkynyl, (4) C1-10 alkoxy, (5) C1-10 alkyl substituted by C1-10 alkoxy, (6) halogen atom, (7) hydroxy, (8) C1-10 alkyl substituted by 1 to 3 halogen atom(s), (9) C1-10 alkyl substituted by C1-10 alkoxy substituted by 1 to 3 halogen atom(s), ring 2, ring 3, ring 4 and ring 5 are each independently (1) cyclic hydrocarbon or (2) heterocyclic ring, ⁃⁃⁃⁃is a single or double bond;

∿ is α-configuration, β-configuration or a mixture thereof, a salt thereof or a cyclodextrin clathrate thereof.

2. A medicament which comprises a combination of the pharmaceutical composition for inhalation comprising the compound represented by formula (I-1-a) according to claim 1, a salt thereof or a cyclodextrin clathrate thereof, and one or more medicament(s) selected from the group consisting of type 4 phosphodiesterase inhibitor, steroids, β-agonist, leukotriene receptor antagonist, thromboxane synthetase inhibitor, thromboxane $A_2$ receptor antagonist, mediator release inhibitor, anti-histamines, xanthine derivative, anticholinergic drugs, cytokine inhibitor, prostaglandins, forskohlin preparation, elastase inhibitor, metalloprotease inhibitor, expectorant, antibiotics and immunosuppressive.

3. A compound represented by formula;(I-1-a):

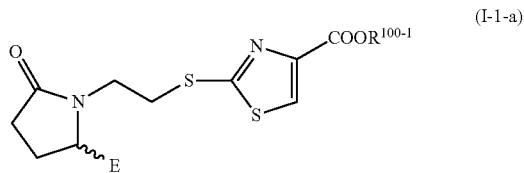

(I-1-a)

wherein $R^{100\text{-}1}$ is C11-20 alkyl which may have a substituent(s), C7-20 alkenyl which may have a substituent(s) or C7-20 alkynyl which may have a substituent(s);

E is $E^1$ or $E^2$, $E^1$ is

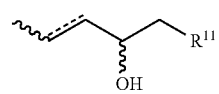

$R^{11}$ is (1) C1-10 alkyl, (2) C1-10 alkylthio, (3) C1-10 alkyl substituted by C3-8 cycloalkyl, (4) C1-10 alkyl substituted by ring 2 or (5) C1-10 alkyl substituted by —$W^1$—$W^2$-ring 2, $W^1$ is (1) —O—, (2) —S—, (3) —SO—, (4) —$SO_2$—, (5) —$NR^{11\text{-}1}$—, (6) carbonyl, (7) —$NR^{11\text{-}1}SO_2$—, (8) carbonylamino or (9) aminocarbonyl, $R^{11\text{-}1}$ is (1) a hydrogen atom, (2) C1-10 alkyl or (3) C2-10 acyl, $W^2$ is (1) a bond or (2) C1-8 alkyl optionally substituted by C1-4 alkyl, a halogen atom or hydroxy, $E^2$ is (1) —$U^1$—$U^2$—$U^3$ or (2) ring 4, $U^1$ is (1) C1-4 alkylene, (2) C2-4 alkenylene, (3) C2-4 alkynylene, (4) -ring 3-, (5) C1-4 alkylene-ring 3-, (6) C2-4 alkenylene-ring 3- or (7) C2-4 alkynylene-ring 3-, $U^2$ is (1) a bond, (2) —$CH_2$—, (3) —CHOH—, (4) —O—, (5) —S—, (6) —SO—, (7) —$SO_2$—, (8) —$NR^{12}$—, (9) carbonyl, (10) —$NR^{12}SO_2$—, (11) carbonylamino or (12) aminocarbonyl, $R^{12}$ is (1) a hydrogen atom, (2) C1-10 alkyl or (3) C2-10 acyl, $U^3$ is (1) C1-8 alkyl optionally substituted by 1 to 3 substituent(s)<selected from C1-10 alkyl, halogen atom, hydroxy, C1-10 alkoxy, C1-10 alkylthio and $NR^{13}R^{14}$, (2) C2-8 alkenyl optionally substituted by 1 to 3 substituent(s) selected from C1-10 alkyl, a halogen atom, hydroxy, C1-10 alkoxy, C1-10 alkylthio and $NR^{13}R^{14}$, (3) C2-8 alkynyl optionally substituted by 1 to 3 substituent(s) selected from C1-10 alkyl, a halogen atom, hydroxy, C1-10 alkoxy, C1-10 alkylthio and $NR^{13}R^{14}$, (4) C1-8 alkyl substituted by ring 4 or (5) ring 4, $R^{13}$ and $R^{14}$ are each independently (1) a hydrogen atom or (2) C1-10 alkyl, ring 2, ring 3 and ring 4 are each independently optionally substituted by 1 to 5 R, R is (1) C1-10 alkyl, (2) C2-10 alkenyl, (3) C2-10 alkynyl, (4) C1-10 alkoxy, (5) C1-10 alkylthio, (6) halogen atom, (7) hydroxy, (8) nitro, (9) —$NR^{15}R^{16}$, (10) C1-10 alkyl substituted by C1-10 alkoxy, (11) C1-10 alkyl substituted by 1 to 3 halogen atom(s), (12) C1-10 alkyl substituted by C1-10 alkoxy substituted by 1 to 3 halogen atom(s), (13) C1-10 alkyl substituted by —$NR^{15}R^{16}$, (14) ring 5, (15) —O-ring 5, (16) C1-10 alkyl substituted by ring 5, (17) C2-10 alkenyl substituted by ring 5, (18) C2-10 alkynyl substituted by ring 5, (19) C1-10 alkoxy substituted by ring 5, (20) C1-10 alkyl substituted by —O-ring 5, (21) —$COOR^{17}$, (22) C1-10 alkoxy substituted by 1 to 4 halogen atom(s), (23) formyl, (24) C1-10 alkyl substituted by hydroxy or (25) C2-10 acyl, $R^{15}$, $R^{16}$ and $R^{17}$ are each independently (1) hydrogen atom or (2) C1-10 alkyl, ring 5 may be substituted by 1 to 3 substituent(s) selected from the following (1) to (9); (1) C1-10 alkyl, (2) C2-10 alkenyl, (3) C2-10 alkynyl, (4) C1-10 alkoxy, (5) C1-10 alkyl substituted by C1-10 alkoxy, (6) halogen atom, (7) hydroxy, (8) C1-10 alkyl substituted by 1 to 3 halogen atom(s), (9) C1-10 alkyl substituted by C1-10 alkoxy substituted by 1 to 3 halogen atom(s), ring 2, ring 3, ring 4 and ring 5 are each independently (1) cyclic hydrocarbon or (2) heterocyclic ring, ⸺ is a single or double bond;

⁓ is α-configuration, β-configuration or a mixture thereof, a salt thereof or a cyclodextrin clathrate thereof.

4. A compound, which is undecyl 2-[(2-{(2R)-2-[(3,5-dichlorophenoxy)methyl]-5-oxo-1-pyrrolidinyl}ethyl)sulfanyl]-1,3-thiazole-4-carboxylate, 10-phenyldecyl 2-[(2-{(2R)-2-[(3,5-dichlorophenoxy)methyl]-5-oxo-1-pyrrolidinyl}ethyl)sulfanyl]-1,3-thiazole-4-carboxylate, 10-phenyldecyl 2-{[2-((5R)-2-oxo-5-{[3-(trifluoromethoxy)phenoxy]methyl}-1-

$E^1$ is

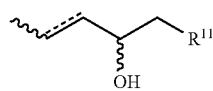

$R^{11}$ is (1) C1-10 alkyl, (2) C1-10 alkylthio, (3) C1-100 alkyl substituted by C3-8 cycloalkyl, (4) C1-10 alkyl substituted by ring 2 or (5) C1-10 alkyl substituted by —$W^1$—$W^2$— ring 2, $W^1$ is (1) —O—, (2) —S—, (3) —SO—, (4) —$SO_2$—, (5) —$NR^{11-1}$—, (6) carbonyl, (7) —$NR^{11-1}SO_2$—, (8) carbonylamino or (9) aminocarbonyl, $R^{11-1}$ is (1) a hydrogen atom, (2) C1-10 alkyl or (3) C2-10 acyl, $W^2$ is (1) a bond or (2) C1-8 alkyl optionally substituted by C1-4 alkyl, a halogen atom or hydroxy, $E^2$ is (1) —$U^1$—$U^2$—$U^3$ or (2) ring 4, $U^1$ is (1) C1-4 alkylene, (2) C2-4 alkenylene, (3) C2-4 alkynylene, (4)-ring 3-, (5) C1-4 alkylene-ring 3-, (6) C2-4 alkenylene-ring 3- or (7) C2-4 alkynylene-ring 3-, $U^2$ is (1) a bond, (2) —$CH_2$—, (3) —CHOH—, (4) —O—, (5) —S—, (6) —SO—, (7) —$SO_2$—, (8) —$NR^{12}$—, (9) carbonyl, (10) —$NR^{12}SO_2$—, (11) carbonylamino or (12) aminocarbonyl, $R^{12}$ is (1) a hydrogen atom, (2) C1-10 alkyl or (3) C2-10 acyl, $U^3$ is (1) C1-8 alkyl optionally substituted by 1 to 3 substituent(s) selected from C1-10 alkyl, halogen atom, hydroxy, C1-10 alkoxy, C1-10 alkylthio and $NR^{13}R^{14}$, (2) C2-8 alkenyl optionally substituted by 1 to 3 substituent(s) selected from C1-10 alkyl, a halogen atom, hydroxy, C1-10 alkoxy, C1-10 alkylthio and $NR^{13}R^{14}$, (3) C2-8 alkynyl optionally substituted by 1 to 3 substituent(s)<selected from C1-10 alkyl, a halogen atom, hydroxy, C1-10 alkoxy, C1-10 alkylthio and $NR^{13}R^{14}$, (4) C1-8 alkyl substituted by ring 4 or (5) ring 4, pyrrolidinyl)ethyl]sulfanyl}-1,3-thiazole-4-carboxylate, undecyl 2-[(2-{(2R)-2-[(heptylamino)methyl]-5-oxo-1-pyrrolidinyl}ethyl)sulfanyl]-1,3-thiazole-4-carboxylate, 10-phenyldecyl 2-[(2-(2R)-2-[(heptylamino)methyl]-5-oxo-1-pyrrolidinyl}ethyl)sulfanyl]-1,3-thiazole-4-carboxylate or 10-phenyldecyl 2-[(2-{(2R)-2-[(1E)-1-nonenyl]-5-oxo-1-pyrrolidinyl}ethyl)sulfanyl]-1,3-thiazole-4-carboxylate, a salt thereof or a cyclodextrin clathrate thereof.

5. A method for treating respiratory disease which is characterized by administrating by inhalation an effective dose of a compound represented by formula (I-1-a) to a subject in need thereof:

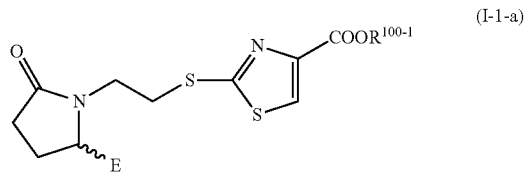

(I-1-a)

wherein $R^{100-1}$ is C11-20 alkyl which may have a substituent(s), C7-20 alkenyl which may have a substituent(s) or C7-20 alkynyl which may have a substituent(s);

E is $E^1$ or $E^2$, $R^{13}$ and $R^{14}$ are each independently (1) a hydrogen atom or (2) C1-10 alkyl, ring 1, ring 2, ring 3 and ring 4 are each independently optionally substituted by 1 to 5 R, R is (1) C1-10 alkyl, (2) C2-10 alkenyl, (3) C2-10 alkynyl, (4) C1-10 alkoxy, (5) C1-10 alkylthio, (6) halogen atom, (7) hydroxy, (8) nitro, (9) —$NR^{15}R^{16}$, (10) C1-10 alkyl substituted by C1-10 alkoxy, (11) C1-10 alkyl substituted by 1 to 3 halogen atom(s), (12)C1-10 alkyl substituted by C1-10 alkoxy substituted by 1 to 3 halogen atom(s), (13) C1-10 alkyl substituted by —NR$^{15}$R$^{16}$, (14) ring 5, (15) —O-ring 5, (16) C1-10 alkyl substituted by ring 5, (17) C2-10 alkenyl substituted by ring 5, (18) C2-10 alkynyl substituted by ring 5, (19) C1-10 alkoxy substituted by ring 5, (20) C1-10 alkyl substituted by —O-ring 5, (21) —COOR$^{17}$, (22) C1-10 alkoxy substituted by 1 to 4 halogen atom(s), (23) formyl, (24) C1-10 alkyl substituted by hydroxy or (25) C2-10 acyl, R$^{15}$, R$^{16}$ and R$^{17}$ are each independently (1) hydrogen atom or (2) C1-10 alkyl, ring 5 may be substituted by 1 to 3 substituent(s) selected from the following (1) to (9); (1) C1-10 alkyl, (2) C2-10 alkenyl, (3) C2-10 alkynyl, (4) C1-10 alkoxy, (5) C1-10 alkyl substituted by C1-10 alkoxy, (6) halogen atom, (7) hydroxy, (8) C1-10 alkyl substituted by 1 to 3 halogen atom(s), (9) C1-10 alkyl substituted by C1-10 alkoxy substituted by 1 to 3 halogen atom(s), ring 2, ring 3, ring 4 and ring 5 are each independently (1) cyclic hydrocarbon or (2) heterocyclic ring, ⁼⁼⁼⁼is a single or double bond;

∿ is α-configuration, β-configuration or a mixture thereof, a salt thereof or a cyclodextrin clathrate thereof, wherein the respiratory disease is asthma, pulmonary injury, pulmonary fibrosis, pulmonary emphysema, bronchitis, chronic obstructive pulmonary disease, adult respiratory distress syndrome, cystic fibrosis or pulmonary hypertension.

\* \* \* \* \*

UNITED STATES PATENT AND TRADEMARK OFFICE
CERTIFICATE OF CORRECTION

PATENT NO. : 7,858,650 B2
APPLICATION NO. : 11/665966
DATED : December 28, 2010
INVENTOR(S) : Shigeki Yamamoto et al.

It is certified that error appears in the above-identified patent and that said Letters Patent is hereby corrected as shown below:

Please correct claim 4 to read as follows:

4. A compound, which is undecyl 2-[(2-{(2R)-2-[(3,5-dichlorophenoxy)methyl]-5-oxo-1-pyrrolidinyl}ethyl)sulfanyl]-1,3-thiazole-4-carboxylate, 10-phenyldecyl 2-[(2-{(2R)-2-[(3,5-dichlorophenoxy)methyl]-5-oxo-1-pyrrolidinyl}ethyl)sulfanyl]-1,3-thiazole-4-carboxylate, 10-phenyldecyl 2-{[2-((5R)-2-oxo-5-{[3-(trifluoromethoxy)phenoxy]methyl}-1-

~~$E^1$ is~~

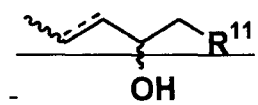

~~$R^{11}$ is (1) C1-10 alkyl, (2) C1-10 alkylthio, (3) C1-100 alkyl substituted by C3-8 cycloalkyl, (4) C1-10 alkyl substituted by ring 2 or (5) C1-10 alkyl substituted by -W$^1$-W$^2$-ring 2,~~

Signed and Sealed this
Sixteenth Day of August, 2011

David J. Kappos
*Director of the United States Patent and Trademark Office*

~~$W^1$ is (1) -O-, (2) -S-, (3) -SO-, (4) -SO$_2$-, (5) -NR$^{11-1}$-, (6) carbonyl, (7) -NR$^{11-1}$SO$_2$-, (8) carbonylamino or (9) aminocarbonyl,~~

~~$R^{11-1}$ is (1) a hydrogen atom, (2) C1-10 alkyl or (3) C2-10 acyl,~~

~~$W^2$ is (1) a bond or (2) C1-8 alkyl optionally substituted by C1-4 alkyl, a halogen atom or hydroxy,~~

~~$E^2$ is (1) -U$^1$-U$^2$-U$^3$- or (2) ring 4,~~

~~$U^1$ is (1) C1-4 alkylene, (2) C2-4 alkenylene, (3) C2-4 alkynylene, (4) -ring 3-, (5) C1-4 alkylene-ring 3-, (6) C2-4 alkenylene-ring 3- or (7) C2-4 alkynylene-ring 3-,~~

~~$U^2$ is (1) a bond, (2) -CH$_2$-, (3) -CHOH-, (4) -O-, (5) -S-, (6) -SO-, (7) -SO$_2$-, (8) -NR$^{12}$-, (9) carbonyl, (10) -NR$^{12}$SO$_2$-, (11) carbonylamino or (12) aminocarbonyl,~~

~~$R^{12}$ is (1) a hydrogen atom, (2) C1-10 alkyl or (3) C2-10 acyl,~~

~~$U^3$ is (1) C1-8 alkyl optionally substituted by 1 to 3 substituent(s) selected from C1-10 alkyl, halogen atom, hydroxy, C1-10 alkoxy, C1-10 alkylthio and NR$^{13}$R$^{14}$, (2) C2-8 alkenyl optionally substituted by 1 to 3 substituent(s) selected from C1-10 alkyl, a halogen atom, hydroxy, C1-10 alkoxy, C1-10 alkylthio and NR$^{13}$R$^{14}$, (3) C2-8 alkynyl optionally substituted by 1 to 3 substituent(s) selected from C1-10 alkyl, a halogen atom, hydroxy, C1-10 alkoxy, C1-10 alkylthio and NR$^{13}$R$^{14}$, (4) C1-8 alkyl substituted by ring 4 or (5) ring 4,~~ pyrrolidinyl)ethyl]sulfanyl}-1,3-thiazole-4-carboxylate, undecyl 2-[(2-{(2R)-2-[(heptylamino)methyl]-5-oxo-1-pyrrolidinyl}ethyl)sulfanyl]-1,3-thiazole-4-carboxylate, 10-phenyldecyl 2-[(2-{(2R)-2-[(heptylamino)methyl]-5-oxo-1-pyrrolidinyl}ethyl)sulfanyl]-1,3-thiazole-4-carboxylate or 10-phenyldecyl 2-[(2-{(2R)-2-[(1E)-1-nonenyl]-5-oxo-1-pyrrolidinyl}ethyl)sulfanyl]-1,3-thiazole-4-carboxylate, a salt thereof or a cyclodextrin clathrate thereof.

UNITED STATES PATENT AND TRADEMARK OFFICE
CERTIFICATE OF CORRECTION

PATENT NO. : 7,858,650 B2
APPLICATION NO. : 11/665966
DATED : December 28, 2010
INVENTOR(S) : Shigeki Yamamoto et al.

It is certified that error appears in the above-identified patent and that said Letters Patent is hereby corrected as shown below:

Column 41, line 53 - Column 42, line 40, please correct claim 4 to read as follows:

4. A compound, which is undecyl 2-[(2-{(2R)-2-[(3,5-dichlorophenoxy)methyl]-5-oxo-1-pyrrolidinyl}ethyl)sulfanyl]-1,3-thiazole-4-carboxylate, 10-phenyldecyl 2-[(2-{(2R)-2-[(3,5-dichlorophenoxy)methyl]-5-oxo-1-pyrrolidinyl}ethyl)sulfanyl]-1,3-thiazole-4-carboxylate, 10-phenyldecyl 2-{[2-((5R)-2-oxo-5-{[3-(trifluoromethoxy)phenoxy]methyl}-1-

~~$E^1$ is~~

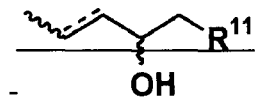

~~$R^{11}$ is (1) C1-10 alkyl, (2) C1-10 alkylthio, (3) C1-100 alkyl substituted by C3-8 cycloalkyl, (4) C1-10 alkyl substituted by ring 2 or (5) C1-10 alkyl substituted by -W¹-W²-ring 2,~~

This certificate supersedes the Certificate of Correction issued August 16, 2011.

Signed and Sealed this
Sixth Day of September, 2011

David J. Kappos
*Director of the United States Patent and Trademark Office*

~~$W^1$ is (1) -O-, (2) -S-, (3) -SO-, (4) -SO$_2$-, (5) -NR$^{11-1}$-, (6) carbonyl, (7) -NR$^{11-1}$SO$_2$-, (8) carbonylamino or (9) aminocarbonyl,~~

~~$R^{11-1}$ is (1) a hydrogen atom, (2) C1-10 alkyl or (3) C2-10 acyl,~~

~~$W^2$ is (1) a bond or (2) C1-8 alkyl optionally substituted by C1-4 alkyl, a halogen atom or hydroxy,~~

~~$E^2$ is (1) -U$^1$-U$^2$-U$^3$- or (2) ring 4,~~

~~$U^1$ is (1) C1-4 alkylene, (2) C2-4 alkenylene, (3) C2-4 alkynylene, (4) -ring 3-, (5) C1-4 alkylene-ring 3-, (6) C2-4 alkenylene-ring 3- or (7) C2-4 alkynylene-ring 3-,~~

~~$U^2$ is (1) a bond, (2) -CH$_2$-, (3) -CHOH-, (4) -O-, (5) -S-, (6) -SO-, (7) -SO$_2$-, (8) -NR$^{12}$-, (9) carbonyl, (10) -NR$^{12}$SO$_2$-, (11) carbonylamino or (12) aminocarbonyl,~~

~~$R^{12}$ is (1) a hydrogen atom, (2) C1-10 alkyl or (3) C2-10 acyl,~~

~~$U^3$ is (1) C1-8 alkyl optionally substituted by 1 to 3 substituent(s) selected from C1-10 alkyl, halogen atom, hydroxy, C1-10 alkoxy, C1-10 alkylthio and NR$^{13}$R$^{14}$, (2) C2-8 alkenyl optionally substituted by 1 to 3 substituent(s) selected from C1-10 alkyl, a halogen atom, hydroxy, C1-10 alkoxy, C1-10 alkylthio and NR$^{13}$R$^{14}$, (3) C2-8 alkynyl optionally substituted by 1 to 3 substituent(s) selected from C1-10 alkyl, a halogen atom, hydroxy, C1-10 alkoxy, C1-10 alkylthio and NR$^{13}$R$^{14}$, (4) C1-8 alkyl substituted by ring 4 or (5) ring 4,~~ pyrrolidinyl)ethyl]sulfanyl}-1,3-thiazole-4-carboxylate, undecyl 2-[(2-{(2R)-2-[(heptylamino)methyl]-5-oxo-1-pyrrolidinyl}ethyl)sulfanyl]-1,3-thiazole-4-carboxylate, 10-phenyldecyl 2-[(2-{(2R)-2-[(heptylamino)methyl]-5-oxo-1-pyrrolidinyl}ethyl)sulfanyl]-1,3-thiazole-4-carboxylate or 10-phenyldecyl 2-[(2-{(2R)-2-[(1E)-1-nonenyl]-5-oxo-1-pyrrolidinyl}ethyl)sulfanyl]-1,3-thiazole-4-carboxylate, a salt thereof or a cyclodextrin clathrate thereof.